US012508350B2

(12) United States Patent
Crouch et al.

(10) Patent No.: US 12,508,350 B2
(45) Date of Patent: Dec. 30, 2025

(54) BREAST PUMP

(71) Applicant: Willow Blossom Holdco Limited, London (GB)

(72) Inventors: Jeremy William Crouch, London (GB); Thomas Michael Malloy, London (GB); Brian McVeigh, London (GB); Christopher James Irlam, London (GB); Jack Cyril Biltcliffe, London (GB); Macdara O'Shea, London (GB); Daniel John Thompson, London (GB)

(73) Assignee: Willow Blossom HoldCo Limited, London (GB)

(*) Notice: Subject to any disclaimer, the term of this patent is extended or adjusted under 35 U.S.C. 154(b) by 0 days.

(21) Appl. No.: 18/418,111

(22) Filed: Jan. 19, 2024

(65) Prior Publication Data

US 2024/0216591 A1 Jul. 4, 2024

Related U.S. Application Data

(63) Continuation of application No. 18/445,455, filed on Aug. 31, 2023.

(30) Foreign Application Priority Data

Aug. 31, 2022 (GB) .................................... 2212671

(51) Int. Cl.
*A61M 1/06* (2006.01)

(52) U.S. Cl.
CPC .................................. *A61M 1/062* (2014.02)

(58) Field of Classification Search
CPC ............................................ A61M 1/06-0697
See application file for complete search history.

(56) References Cited

U.S. PATENT DOCUMENTS

| | | | |
|---|---|---|---|
| 11,135 | A | 6/1854 | Needham |
| 949,414 | A | 2/1910 | Cunningham |
| 2,849,881 | A | 9/1958 | Anderson |
| 3,840,012 | A | 10/1974 | Rushton, Jr. |
| 4,263,912 | A | 4/1981 | Adams |
| 4,270,538 | A | 6/1981 | Murphy |

(Continued)

FOREIGN PATENT DOCUMENTS

| | | | |
|---|---|---|---|
| CN | 2452494 | Y | 10/2001 |
| CN | 1799436 | A | 7/2006 |

(Continued)

OTHER PUBLICATIONS

Declaration of Ryan Bauer In Support of Petition for Inter Partes Review of U.S. Pat. No. 11,413,380, Exhibit 1005 in IPR2024-00953, May 31, 2024; 137 pages.

(Continued)

*Primary Examiner* — Courtney B Fredrickson

(57) ABSTRACT

An in-bra wearable breast pump is provided. The breast pump includes an air pump system for generating a base level vacuum and a pumping vacuum, a breast shield for receiving a user's breast and having a first side and a second side, a first channel for drawing the base level vacuum on the first side of the breast shield, and a second channel for drawing the pumping vacuum on the second side of the breast shield.

22 Claims, 22 Drawing Sheets

(56) References Cited

U.S. PATENT DOCUMENTS 4,390,024 A 6/1983 Williams
4,535,627 A 8/1985 Prost et al.
4,673,388 A 6/1987 Schlensog et al.
4,772,262 A 9/1988 Grant et al.
4,857,051 A 8/1989 Larsson
4,929,229 A 5/1990 Larsson
5,406,063 A 4/1995 Jelen
5,474,683 A 12/1995 Bryant et al.
5,514,166 A 5/1996 Silver et al.
5,542,921 A 8/1996 Meyers et al.
5,571,084 A 11/1996 Palmer
5,941,847 A 8/1999 Huber et al.
5,954,690 A 9/1999 Larsson
5,973,770 A 10/1999 Carter et al.
6,045,529 A 4/2000 Nuesch
6,090,065 A 7/2000 Giles
6,227,936 B1 5/2001 Mendoza
6,257,070 B1 7/2001 Giallorenzo et al.
6,328,709 B1 12/2001 Hung et al.
6,358,226 B1 3/2002 Ryan
6,379,327 B2 4/2002 Lundy
6,383,163 B1 5/2002 Kelly et al.
6,440,100 B1 8/2002 Prentiss et al.
6,461,324 B1 10/2002 Schlensog
6,547,756 B1 4/2003 Greter et al.
6,579,258 B1 6/2003 Atkin et al.
6,652,484 B1 11/2003 Hunckler et al.
6,663,587 B2 12/2003 Silver et al.
6,673,036 B1 1/2004 Britto
6,749,582 B2 6/2004 Britto et al.
6,840,918 B1 1/2005 Britto et al.
6,887,210 B2 5/2005 Quay
7,048,519 B2 5/2006 Fong et al.
7,201,735 B2 4/2007 Atkin et al.
7,223,255 B2 5/2007 Myers et al.
D548,831 S 8/2007 Charlez
7,312,554 B2 12/2007 Vogeley
7,314,400 B2 1/2008 Fildan et al.
7,347,089 B1 3/2008 Kelley et al.
7,559,915 B2 7/2009 Dao et al.
7,641,629 B2 1/2010 Yuen
7,662,018 B1 2/2010 Thompson
7,666,162 B2 2/2010 Renz et al.
7,776,008 B2 8/2010 Renz et al.
7,833,190 B1 11/2010 Hall
7,875,000 B2 1/2011 Krebs et al.
8,057,425 B1 11/2011 Myers et al.
8,118,772 B2 2/2012 Dao et al.
8,187,227 B2 5/2012 Luzbetak et al.
8,216,179 B2 7/2012 Bosshard et al.
8,262,606 B2 9/2012 Greter et al.
8,282,596 B2 10/2012 Greter et al.
8,376,986 B2 2/2013 Van et al.
8,608,685 B2 12/2013 Tashiro et al.
8,702,646 B2 4/2014 Garbez et al.
8,801,495 B1 8/2014 Guindon
8,876,760 B2 11/2014 Bosman et al.
8,926,556 B2 1/2015 Van et al.
9,033,913 B2 5/2015 Khalil et al.
9,173,587 B2 11/2015 Van et al.
9,345,274 B1 5/2016 Prill
9,498,565 B2 11/2016 Nowroozi et al.
9,539,377 B2 1/2017 Makower et al.
9,580,863 B2 2/2017 Bader et al.
D788,293 S 5/2017 Eckstein et al.
D809,646 S 2/2018 Mason et al.
9,919,084 B2 3/2018 Pollen et al.
10,039,871 B2 8/2018 Pollen et al.
10,046,097 B2 8/2018 Thompson et al.
D832,995 S 11/2018 Mason et al.
10,149,929 B2 12/2018 Furrer et al.
10,195,321 B2 2/2019 Tatterfield et al.
10,335,525 B2 7/2019 Felber et al.
10,398,816 B2 9/2019 Chang et al.
10,625,005 B2 4/2020 Chang et al.
10,660,995 B2 5/2020 Makower et al.
D888,225 S 6/2020 Askem et al.
10,864,306 B2 12/2020 Fujisaki
10,881,766 B2 1/2021 O'Toole et al.
10,926,011 B2 2/2021 O'Toole et al.
10,987,455 B2 4/2021 Aalders et al.
11,260,151 B2 3/2022 O'Toole et al.
11,311,654 B2 4/2022 O'Toole et al.
11,324,866 B2 5/2022 O'Toole et al.
11,357,893 B2 6/2022 O'Toole et al.
11,357,894 B2 6/2022 O'Toole et al.
11,376,352 B2 7/2022 O'Toole et al.
11,413,380 B2 8/2022 O'Toole et al.
11,717,599 B2 8/2023 Miller et al.
11,806,454 B2 11/2023 De Becdelievre et al.
2001/0044593 A1 11/2001 Lundy
2002/0062103 A1 5/2002 Larsson et al.
2002/0193731 A1 12/2002 Myers et al.
2002/0198489 A1 12/2002 Silver et al.
2003/0069536 A1 4/2003 Greter et al.
2003/0191433 A1 10/2003 Prentiss
2004/0024351 A1 2/2004 Greter et al.
2004/0056641 A1 3/2004 Myers et al.
2004/0074281 A1 4/2004 Lobdell et al.
2004/0087898 A1 5/2004 Weniger
2004/0127845 A1 7/2004 Renz et al.
2004/0267215 A1 12/2004 Charlez et al.
2005/0154349 A1 7/2005 Renz et al.
2005/0219302 A1 10/2005 Vogeley
2005/0228342 A1 10/2005 Yuen
2005/0245860 A1 11/2005 Britto et al.
2006/0106334 A1 5/2006 Jordan et al.
2006/0111664 A1 5/2006 Samson et al.
2006/0122575 A1 6/2006 Wakabayashi
2007/0051172 A1 3/2007 Perinet et al.
2007/0051727 A1 3/2007 Holley
2007/0054651 A1 3/2007 Farmer et al.
2007/0060873 A1 3/2007 Hiraoka et al.
2007/0135761 A1 6/2007 Cheng et al.
2007/0179439 A1 8/2007 Vogelin et al.
2007/0219486 A1 9/2007 Myers et al.
2007/0228059 A1 10/2007 Karsan
2007/0236584 A1 10/2007 Frost-Ruebling et al.
2008/0009815 A1 1/2008 Grabenkort et al.
2008/0090444 A1 4/2008 Luzbetak et al.
2008/0171970 A1 7/2008 Luzbetak et al.
2008/0177224 A1 7/2008 Kelly et al.
2008/0255503 A1 10/2008 Quackenbush et al.
2008/0262420 A1 10/2008 Dao et al.
2008/0275386 A1 11/2008 Myers
2008/0299517 A1 12/2008 Delaney, II
2009/0254028 A1 10/2009 Brittner
2009/0281482 A1 11/2009 Baker et al.
2009/0281485 A1 11/2009 Baker et al.
2010/0292636 A1 11/2010 Renz et al.
2011/0004154 A1 1/2011 Van Schijndel et al.
2011/0009824 A1 1/2011 Yodfat et al.
2011/0071466 A1 3/2011 Silver et al.
2011/0144636 A1 6/2011 Alexander et al.
2011/0196291 A1 8/2011 Vischer et al.
2011/0274566 A1 11/2011 Amirouche et al.
2012/0021068 A1 1/2012 Barness et al.
2012/0035951 A1 2/2012 Goetz et al.
2012/0043065 A1 2/2012 Ranne et al.
2012/0072117 A1 3/2012 Loddoch et al.
2012/0072118 A1 3/2012 Mann
2012/0095599 A1 4/2012 Pak et al.
2012/0109083 A1 5/2012 Coulthard et al.
2012/0116299 A1 5/2012 Tack
2012/0136325 A1 5/2012 Allen et al.
2012/0143879 A1 6/2012 Stoitsev
2012/0165729 A1 6/2012 Cudworth
2012/0220753 A1 8/2012 Gera et al.
2012/0277636 A1 11/2012 Blondheim et al.
2012/0277728 A1 11/2012 Weber et al.
2013/0023821 A1* 1/2013 Khalil .................. A61M 1/064
604/74
2013/0123688 A1 5/2013 Bosman et al.

(56) References Cited

U.S. PATENT DOCUMENTS

2014/0031744 A1* 1/2014 Chen .................... A61M 1/066 604/74
2014/0052056 A1 2/2014 Garbez et al.
2014/0135683 A1 5/2014 Hradisky et al.
2014/0142501 A1 5/2014 Clark et al.
2014/0227112 A1 8/2014 Felber
2014/0263611 A1 9/2014 Bauer
2014/0275857 A1 9/2014 Toth et al.
2014/0288466 A1 9/2014 Alvarez et al.
2014/0323962 A1 10/2014 Kooijker et al.
2014/0378895 A1 12/2014 Barack
2015/0157775 A1 6/2015 Hu
2015/0212036 A1 7/2015 Jin et al.
2015/0212037 A1 7/2015 Okazaki et al.
2015/0217033 A1 8/2015 Pollen et al.
2015/0217035 A1 8/2015 Pollen et al.
2015/0217036 A1 8/2015 Pollen et al.
2015/0217037 A1 8/2015 Pollen et al.
2015/0283311 A1 10/2015 Alvarez et al.
2015/0314053 A1 11/2015 Furrer et al.
2015/0328380 A1 11/2015 Furrer et al.
2015/0335800 A1 11/2015 Yamashita
2016/0000980 A1 1/2016 Alvarez et al.
2016/0058928 A1 3/2016 Nowroozi et al.
2016/0058929 A1 3/2016 Medvedev et al.
2016/0082165 A1 3/2016 Alvarez et al.
2016/0082166 A1 3/2016 Guthrie et al.
2016/0135998 A1 5/2016 Riesinger
2016/0151551 A1 6/2016 Felber
2016/0158424 A1 6/2016 Chen et al.
2016/0166745 A1 6/2016 Aalders
2016/0174728 A1 6/2016 Karp et al.
2016/0206794 A1* 7/2016 Makower ............ A61M 1/0697
2016/0213824 A1 7/2016 Fridman
2016/0220743 A1 8/2016 Guthrie et al.
2016/0220745 A1 8/2016 Guthrie et al.
2016/0228625 A1 8/2016 Holtz et al.
2016/0256617 A1 9/2016 Hansen
2016/0271305 A1 9/2016 Kurihara et al.
2016/0287767 A1 10/2016 Simmons et al.
2016/0296681 A1 10/2016 Gaskin et al.
2016/0296682 A1 10/2016 Phillips et al.
2016/0304004 A1 10/2016 Sandbothe et al.
2016/0310650 A1 10/2016 Makower et al.
2016/0325031 A1* 11/2016 Miller ................ A61M 39/223
2017/0021068 A1 1/2017 Gaskin et al.
2017/0035951 A1 2/2017 Tanaka
2017/0043065 A1 2/2017 Takeuchi
2017/0072117 A1 3/2017 Kurihara et al.
2017/0072118 A1 3/2017 Makower et al.
2017/0080135 A1 3/2017 Chen
2017/0095599 A1 4/2017 Kondo et al.
2017/0112983 A1 4/2017 Thorne et al.
2017/0136161 A1 5/2017 Alvarez et al.
2017/0143879 A1 5/2017 Okaguchi
2017/0173232 A1 6/2017 Chang et al.
2017/0173233 A1 6/2017 Tanaka
2017/0216505 A1* 8/2017 Kim .................... A61M 1/0697
2017/0220753 A1 8/2017 Guthrie et al.
2017/0292509 A1 10/2017 Kurihara et al.
2018/0008758 A1* 1/2018 Garbez ................ A61M 39/22
2018/0021490 A1 1/2018 Chang et al.
2018/0021491 A1 1/2018 Rigert et al.
2018/0028733 A1 2/2018 Rigert et al.
2018/0104396 A1 4/2018 Park
2018/0110900 A1 4/2018 Korenfeld
2018/0110906 A1 4/2018 Barack
2018/0154055 A1 6/2018 Alvarez et al.
2018/0333523 A1 11/2018 Chang et al.
2018/0361040 A1 12/2018 O'Toole et al.
2019/0209748 A1 7/2019 Analytis et al.
2019/0275222 A1* 9/2019 Evans .................. A61M 1/064
2019/0365966 A1 12/2019 Bächler et al.
2020/0016307 A1 1/2020 Edelman et al.
2020/0300237 A1 9/2020 Marbet et al.
2021/0030934 A1 2/2021 Zhang
2021/0077673 A1 3/2021 Mason et al.
2021/0093761 A1* 4/2021 Hwang ................. A61M 39/22
2021/0170080 A1 6/2021 O'Toole et al.
2021/0196873 A1 7/2021 O'Toole et al.
2021/0196874 A1 7/2021 O'Toole et al.
2021/0196875 A1 7/2021 O'Toole et al.
2021/0196876 A1 7/2021 O'Toole et al.
2021/0205511 A1 7/2021 O'Toole et al.
2021/0205512 A1 7/2021 O'Toole et al.
2021/0205513 A1 7/2021 O'Toole et al.
2021/0205514 A1 7/2021 O'Toole et al.
2021/0205515 A1 7/2021 O'Toole et al.
2021/0205516 A1 7/2021 O'Toole et al.
2021/0205517 A1 7/2021 O'Toole et al.
2021/0205518 A1 7/2021 O'Toole et al.
2021/0228789 A1 7/2021 O'Toole et al.
2021/0268158 A1 9/2021 O'Toole et al.
2022/0031918 A1* 2/2022 Quackenbush ....... A61M 39/24
2022/0409782 A1* 12/2022 Höner .................... A61M 1/06
2023/0111110 A1 4/2023 De Becdelievre et al.
2023/0143842 A1 5/2023 O'Toole et al.
2023/0158215 A1 5/2023 De Becdelievre et al.
2023/0338630 A1 10/2023 Claassen et al.

FOREIGN PATENT DOCUMENTS

CN 101549180 A 10/2009
CN 105233355 A 1/2016
CN 105288759 A 2/2016
CN 205626591 U 10/2016
CN 205913571 U 2/2017
CN 206473606 U 9/2017
CN 109621041 A 4/2019
CN 209033304 U 6/2019
CN 210096493 U 2/2020
DE 3311982 C2 12/1986
DE 19750620 A1 6/1999
EP 0503280 A2 9/1992
EP 1586340 A2 10/2005
EP 1430918 B1 5/2008
EP 2436277 A1 4/2012
EP 2502640 A1 9/2012
EP 2210628 B1 2/2013
EP 1404393 B1 12/2014
EP 2077868 B1 7/2016
EP 1263487 B2 11/2016
EP 3299043 A1 3/2018
EP 3482782 A1 5/2019
EP 4000661 A1 5/2022
GB 2435617 B 3/2008
GB 2473022 B 12/2011
GB 2499248 B 4/2014
JP H11178917 A 7/1999
JP 2000350527 A 12/2000
JP 2007501673 A 2/2007
JP 2013545519 A 12/2013
JP 2014529312 A 11/2014
JP 2014532498 A 12/2014
JP 2016010524 A 1/2016
JP 2016508804 A 3/2016
JP 2016514516 A 5/2016
JP 2016524490 A 8/2016
JP 2016526396 A 9/2016
JP 2017503552 A 2/2017
JP 2017509379 A 4/2017
JP 6292720 B2 3/2018
RU 2344380 C1 1/2009
RU 2441367 C2 2/2012
WO WO 1990000413 A1 1/1990
WO WO-9420158 A1 9/1994
WO WO-9625187 A1 8/1996
WO WO-9636298 A1 11/1996
WO WO 2002102437 A2 12/2002
WO WO-2004108184 A2 12/2004
WO WO-2005079441 A2 9/2005
WO WO-2005114113 A2 12/2005
WO WO-2005114116 A1 12/2005
WO WO-2005114113 A3 3/2006

(56) References Cited

FOREIGN PATENT DOCUMENTS

| | | | |
|---|---|---|---|
| WO | WO 2008137678 | A1 | 11/2008 |
| WO | WO-2009134271 | A1 | 11/2009 |
| WO | WO-2013064852 | A1 | 5/2013 |
| WO | WO-2014094187 | A1 | 6/2014 |
| WO | WO-2014160614 | A1 | 10/2014 |
| WO | WO-2015069095 | A1 | 5/2015 |
| WO | WO-2015081459 | A1 | 6/2015 |
| WO | WO-2015116749 | A1 | 8/2015 |
| WO | WO-2015120321 | A1 | 8/2015 |
| WO | WO-2015150225 | A1 | 10/2015 |
| WO | WO-2015174330 | A1 | 11/2015 |
| WO | WO-2016002606 | A1 | 1/2016 |
| WO | WO-2016006458 | A1 | 1/2016 |
| WO | WO-2016006494 | A1 | 1/2016 |
| WO | WO-2016006496 | A1 | 1/2016 |
| WO | WO-2016007560 | A1 | 1/2016 |
| WO | WO-2016007561 | A1 | 1/2016 |
| WO | WO-2016010524 | A1 | 1/2016 |
| WO | WO-2016014469 | A1 | 1/2016 |
| WO | WO-2016014488 | A1 | 1/2016 |
| WO | WO 2016014494 | A1 | 1/2016 |
| WO | WO-2016024558 | A1 | 2/2016 |
| WO | WO-2016025405 | A1 | 2/2016 |
| WO | WO-2016039083 | A1 | 3/2016 |
| WO | WO-2016104673 | A1 | 6/2016 |
| WO | WO-2016108616 | A1 | 7/2016 |
| WO | WO-2016164853 | A1 | 10/2016 |
| WO | WO-2016186452 | A1 | 11/2016 |
| WO | WO-2017061349 | A1 | 4/2017 |
| WO | WO-2017108555 | A1 | 6/2017 |
| WO | WO 2017139437 | A1 | 8/2017 |
| WO | WO-2017139480 | A1 | 8/2017 |
| WO | WO-2017190678 | A1 | 11/2017 |
| WO | WO 2018054758 | A1 | 3/2018 |
| WO | WO-2018229504 | A1 | 12/2018 |
| WO | WO 2019080995 | A1 | 5/2019 |

OTHER PUBLICATIONS

4MD Medical, "Assembling Spctra Breast Pump Parts," YouTube [online], dated Nov. 13, 2016, URL: http:// www.youtube.com/watch?v=ChV8xQfcBxU, 3 pages.

Amended Complaint in *Shenzhen Root Technology Co., Ltd.* v. *Chiaro Technology, Ltd.*, WDWA-2-23-cv-00631, filed Jun. 2, 2023; 24 pages.

Extended European Search Report issued in European Application No. 22174446.9, mailed Oct. 11, 2022, 26 pages.

GB Search Report, dated Nov. 15, 2017, issued in priority GB Application No. GB1709561.3, 4 pages.

GB Search Report, dated Nov. 28, 2017, issued in priority GB Application No. GB1709566.2, 3 pages.

GB Search Report for , dated Nov. 29, 2017, issued in priority GB Application No. GB1709564.7, 4 pages.

International Search Report issued in International Application No. PCT/GB2021/050764, mailed Jul. 6, 2021, 5 pages.

International Search Report issued in PCT/GB2018/051659 dated Dec. 4, 2018, 9 pages.

Japanese Search Report issued in Japanese Application No. 2020519188, mailed Jun. 24, 2022, 20 pages.

The Best Hands-Free Breast Pumps, posted at healthline.com, earliest date posted on Aug. 24, 2020, [online], acquired on Oct. 30, 2021, Available on internet. url: https://www.healthline.com/health/parenting/breast-feeding/best-hands-free-breast-pumps#Best-hands-free-breast-pumps (Year: 2020), 11 pages.

Whisper Wear Hands-Free Breast Pump, Model:WWWPMP01, UserGuide, pp. 1-20 , Distributed with product atleast as early as 2007 (see https://web.archive.org/web/20070621162539/http://www.whisperwear.com/pump_single.html ), 10 pages.

Amended Claims in Response to Rule 71(3) (clean) regarding European Patent Application No. 18741597.1 to Positec Power Tools (Suzhou) Co. Ltd; dated Feb. 20, 2024; 4 pages.

Breastfeeding and the Use of Human Milk, American Academy of Pediatrics, Pediatrics, vol. 100, No. 6, Dec. 6, 1997; pp. 1035-1039.

Courage, Katherine, "The Sucky History of the Breast Pump," Innovation, Smithsonian Magazine, Sep. 12, 2022; 17 pages. Available at: https://www.smithsonianmag.com/innovation/sucky-history-of-the-breast-pump-180980653/.

GB 201709566.2 entitled 'Breast Pump' filed Jun. 15, 2017; 44 pages (Priority Document 1).

GB201709564.7 entitled 'A Liquid Level Measurement System' filed Jun. 15, 2017; 24 pages (Priority Document 2).

GB 201709561.3 entitled 'Bra Clip' filed Jun. 15, 2017; 24 pages (Priority Document 3).

GB 201809036.5 entitled 'Breast Pump System' filed Jun. 1, 2018; 169 pages (Priority Document 4).

Illinois Nursing Mothers in the Workplace Act, Illinois General Assembly, Jul. 12, 2001; 2 pages. Available at: https://www.ilga.gov/legislation/ilcs/ilcs3.asp?ActID=2429.

Omnexus, "Silicone Rubber: Complete Guide on Highly Durable Elastomer" Feb. 28, 2024, [cited Feb. 28, 2024] Available from: [https://omnexus.specialchem.com/selection-guide/silicone-rubber-elasto].

Reply to communication under Rule 71(3) regarding European Patent Application No. 18741597.1 to Positec Power Tools (Suzhou) Co. Ltd, dated Feb. 20, 2024; 1 page.

Sex Descrimination—Breastfeeding and Expressing Milk, British Columbia Human Righs Commission Policy and Procedure Manual, Aug. 1, 2000; 2 pages. Available at: http://www.infactcanada.ca/br_bc_humanrights.htm.

Women's Health Today, "How to Choose a Breast Pump" Nov. 8. 2017, 8 pages; Available from: [https://womenshealthtoday.blog/2017 /11 /08/how-to-choose-a-breast-pump/] original file name: D2 How to Choose a Breast Pump_Womens Health Today.pdf.

Wyatt, Stephanie, MSN, APN, "Challenges of the Working Breastfeeding Mother, Workplace Solutions," AAOHN Journal, vol. 50, No. 2, Feb. 2022; pp. 61-66.

Exhibit List for IPR 2024-01296 (Declaration of Ryan Bauer U.S. Pat. No. 11,413,380) Feb. 14, 2024, 142 pages.

International Search Report and Written Opinion for Application No. PCT/EP2023/073973, mailed on Dec. 4, 2023, 9 pages.

International Search Report and Written Opinion for Application No. PCT/EP2023/073975, mailed on Dec. 19, 2023, 9 pages.

CNET, "Pump on the go with the willow breast pump" 4 pages.

D'Ignazio, C., et al., "A Feminist HCI Approach to Designing Postpartum Technologies: When I first saw a breast pump I was wondering if it was a joke," Proceedings of the 2016 CHI Conference on Human Factors in Computing Systems, Association for Computing Machinery, San Jose, California, USA, 11 pages (May 2016).

Falcone, J., "CES 2017: The final word" CNET, 18 pages (2017).

Ingraham, N., "How a smart breast pump won CES," Engadget, 11 pages.

Larson, S., "Smart breast pump lets moms multitask," CES 2017: Willow's smart breast pump lets moms multitask, 16 pages.

Laughlin, S., "Willow is among several companies at CES focused on meeting the needs of new moms," CES 2017: Maternal tech, 6 pages (Jan. 2017).

Martin, C. E., and Cary, J., "Shouldn't the Breast Pump Be as Elegant as an iPhone and as Quiet as a Prius by Now?" Motherlode: Adventures in Parenting, 3 pages (Mar. 2014).

"Medela Pump In Style Advanced—Review" The Pumping mommy, 8 pages.

Strauss, E., "Breast Pumps Are Finally Getting Better. Here's How," Slate, 7 pages (May 2016).

"The Breast Pump Finally Joins the 21st Century," Arielle Pardes, 18 pages (2017).

The Willow smart breast pump could be a game-changer for moms, 2 pages.

Willow breast pump at CES 2017, 2 pages.

Declaration of Ryan Bauer in Support of Request for Reexamination of U.S. Pat. No. 11,357,893 Under 35 U.S.C. § 302 and 37 C.F.R.

(56) References Cited

OTHER PUBLICATIONS

§ 1.510, in the United States Patent and Trademark Office, Sep. 24, 2024; 233 pages.

* cited by examiner

BREAST PUMP

CROSS-REFERENCE TO RELATED APPLICATIONS

The present application is a continuation of U.S. application Ser. No. 18/445,455, filed Aug. 31, 2023, which claims priority to GB Application No. 2212671.8, filed Aug. 31, 2022, which are incorporated herein by reference in their entirety.

FIELD

The present disclosure relates to a breast pump and, in particular, to an in-bra wearable breast pump for expressing human milk.

BACKGROUND

A breast pump system is a mechanical or electro-mechanical device that extracts milk from the breasts of a lactating person.

Breast pumps for expressing human breast milk are known. A vacuum is used to simulate suction generated by a feeding child. Essentially, there are two different types of breast pumps: the first is manually operated, i.e. the vacuum required for expressing is generated by manual actuation of a vacuum pump. In the second type, an electric pump assembly is present, having an electric motor for generating the necessary vacuum.

A typical electric breast pump design is as shown in WO 96/25187 A1. A large suction generating device is provided, which is freestanding. This is attached by air lines to one or two breast shields which engage with the user's breasts. A pressure cycle is applied from the suction generating device, via the air lines, to the breast shields. This generates a pressure cycle on the user's breasts to simulate the suction generated by a feeding child.

Fully integrated wearable breast pump systems are known in the art. In such pump systems, the suction source, power supply and milk container are contained in a single, wearable device and there is no need for bulky external components or connections. Such devices can be provided with a substantially breast shaped convex profile so as to fit within a user's bra for discreet pumping, as well as pumping on-the-go without any tethers to electrical sockets or collection stations. The internal breast shield is convex to fit over a breast.

WO2018229504, which is hereby incorporated by reference in its entirety, describes a wearable breast pump system including a housing shaped, at least in part, to fit inside a bra and a piezo air-pump. The piezo air-pump is fitted in the housing and forms part of a closed loop system that drives a separate, deformable diaphragm to generate negative air pressure. The diaphragm is removably mounted on a breast shield.

Many portable breast pump solutions are loud, prone to leakage and do not produce as high milk production efficiency as non-portable breast pumps. In view of the above, there is a need for an improved breast pump.

SUMMARY

There is provided a breast pump as defined in the disclosure and in the appended claims.

BRIEF DESCRIPTION OF THE DRAWINGS

Specific embodiments are described below by way of example only and with reference to the accompanying drawings in which.

Aspects and features of embodiments of the present invention are set out in the accompanying claims.

DETAILED DESCRIPTION OF THE EMBODIMENTS

Figure 19:
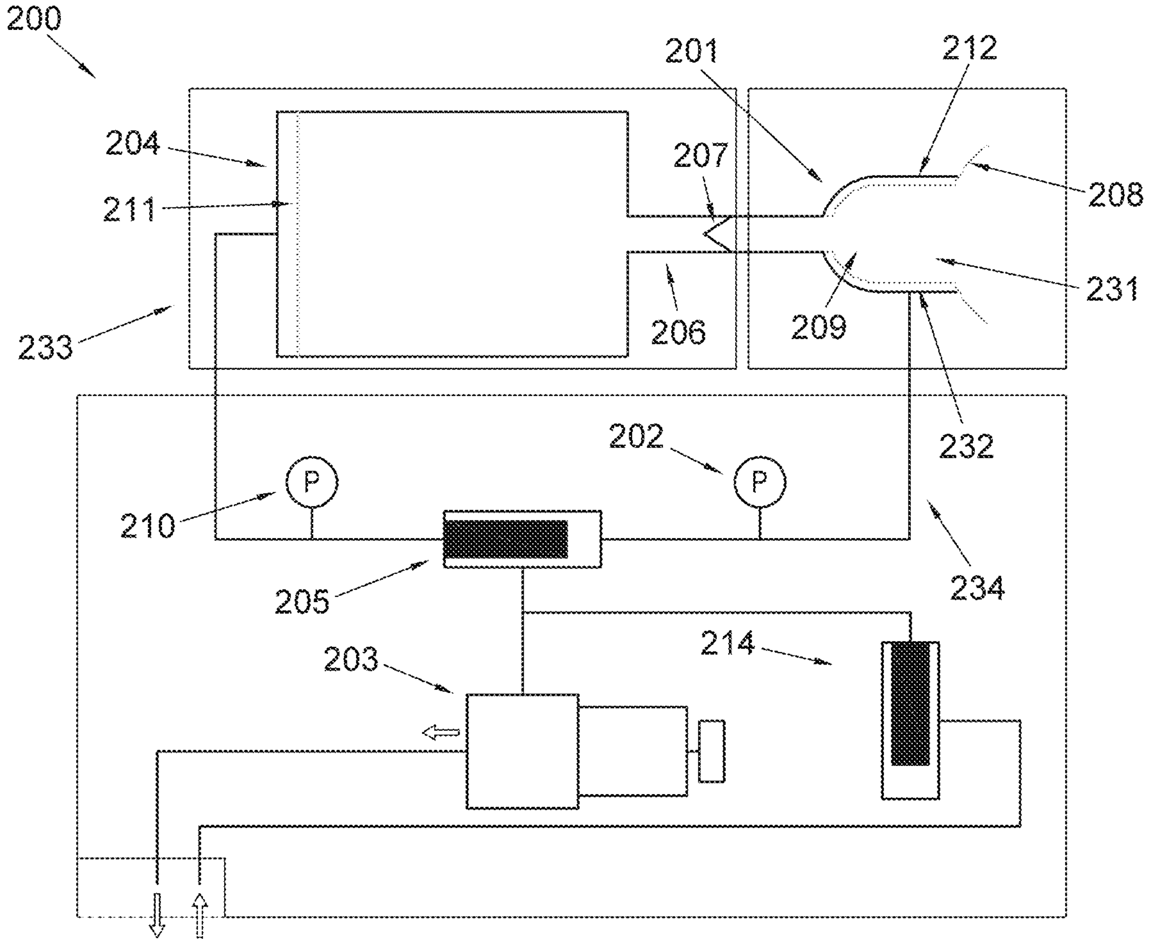
FIG. 19 shows a breast pump according to an embodiment of the present invention.

A breast pump 100 according to the embodiment of the present invention is shown in FIGS. 1 to 13. FIGS. 1 to 13 show a process of how the base level vacuum may be generated and maintained throughout a pumping cycle and whole pumping sessions. A breast pump 200 according to another embodiment of the present invention is shown in FIG. 19.

Components of the system will be described with reference to FIG. 1*a*, then operation of the breast pump will be described with relation to the steps shown in FIGS. 1*a* to 13.

The breast pump 100 is a kind suitable for expressing human breast milk. The assembled breast pump 100 system may comprise a housing (shown in FIG. 14, 121) shaped to substantially fit inside a bra. The housing may be designed to enclose all the components of the breast pump 100 shown in FIGS. 1 to 13. The housing may be shaped to discreetly fit underneath a user's clothing or to be worn inside a bra. The housing may comprise a breast shield 101 for fitting to a user's breast 102, at least one air-pump 103 for generating a vacuum, a milk container 104. The housing may also comprise a rechargeable battery and control electronics (not shown). The breast pump 100 may be configured as a self-contained, in-bra wearable device. The breast shield 101 and milk container 104 may also be configured as being in-bra wearable.

In the embodiments shown in FIGS. 1*a* to 13 and 19, all the components are configured to fit into a bra. In other embodiments, some components may be outside the bra, for example, the pump.

In some embodiments, the only parts of the system that come into contact with milk in normal use are the breast shield 101 and the milk container 104 and any portion of the breast pump 100 which connects the breast shield 101 and the milk container 104, such as a nipple tunnel 109 and non-return valve 107. In one embodiment, milk only flows along a milk path through the breast shield 101 and then directly into the milk container 104. In this embodiment, milk does not contact any part of the housing, for maximum hygiene and ease of cleaning.

The breast shield 101 and the milk container 104 may be directly removable from or attachable to the housing in normal use or during normal dis-assembly. All other parts that are user-removable in normal use or during normal dis-assembly may be attached to either the breast shield 101 or the milk container 104. The breast shield 101 and milk container 104 may be removed or attached from the housing, for example, using a one click or one press action or a push button or any other release mechanism such as magnetic or screw attachments. Audible and/or haptic feedback may confirm that the pump is properly assembled.

The modularity of the breast pump 100 allows for easy assembly, disassembly and replacement of different parts such as the breast shield 101 and milk collection container. This also allows for different parts of the pump to be easily washed and/or sterilised. The breast shield 101 and container assembly, both of which are in contact with milk during pumping, may therefore be efficiently and easily cleaned; in some embodiments, these are the only two items that need to be cleaned due to contact with breast milk; in particular, the housing does may not need to be cleaned.

Base Level Vacuum

The breast pump 100 of some embodiments disclosed herein is able to achieve a base level vacuum throughout a whole pumping cycle. This means that a constant level of vacuum is produced to enable the breast pump 100 to maintain contact with the user's breast 102 at all times during the pumping process. The base level vacuum means that the pressure applied to the user's breast 102 never reaches or rises above atmospheric pressure. Instead, a constant negative air pressure is achieved to maintain contact between the user's breast 102 and the breast shield 101. The base level vacuum provides a feeling of biomimicry, as though a child is latched on throughout the pumping process, which can reassure the user that the breast pump 100 is securely attached. This also provides a seal between the breast and the breast shield 101 at all times during the pumping cycle, therefore, reducing the likelihood of milk leaking from the breast shield 101. This offers the additional benefits of sealing the device to the user's breast 102 to offer a reassuring fit and tactile confirmation that the device is firmly in place. The base level vacuum is also applied to expel all redundant air within the breast shield. This minimises the possible amount of air volume on the wet side of the system to make the best use of the pump system acting on the reduced volume of air.

The desired pressure of the base level vacuum may be individual to the user as what the user perceives to be strong enough to maintain a secure seal against the breast throughout the pumping session but without becoming uncomfortable.

The desired pressure of the base level vacuum can be tuned to a user's requirements and may be from −15 to −70 mmHg (relative to atmospheric pressure). In one embodiment, the desired pressure of the base level vacuum is from −30 to −60 mmHg (relative to atmospheric pressure). In another embodiment, the desired pressure of the base level vacuum is −50 mmHg (relative to atmospheric pressure), plus or minus 10%. An upper limit of the desired pressure of the base level vacuum may be −15 mmHg, since at levels any higher than this, the base level vacuum may be at risk of breaking due to either insufficient hold to the breast, or a large milk ejection which causes the base level vacuum to decay faster than it is topped up again. The lower limit of the base level vacuum may be −100 mmHg since this is considered to be the limit of what a user would find comfortable throughout an entire pumping session. The user can be given the option to choose a desired base level vacuum, for example, of either −25 mmHg, −50 mmHg or −75 mmHg (relative to atmospheric pressure), although other known values may be chosen. This option can be displayed to a user via a graphical user interface on a digital application.

Air Pump

The air pump 103 may be a mechanical air pump 103 designed to either extract air from a breast pump 100 system or insert air into a breast pump 100 system. In some embodiments of the present invention, the air pump 103 is configured to draw air out of the breast pump 100 system and create a negative air pressure in the nipple tunnel 109. When the air pump 103 is activated, negative air pressure differential is created between the air pump 103, the two diaphragms 111 and 112, such as those in the milk container

104 and/or the breast shield 101, thereby applying negative pressure differential to the nipple, drawing milk from the breast, and collecting it inside the milk container 104.

A negative air pressure differential is defined as any pressure below that of the surrounding air environment. In other words, a negative air pressure differential is a pressure lower than the system of the breast pump 100 when the air pump 103 is not in use. A typical air pressure, or atmospheric pressure, of a standard environment is 760 mmHg, therefore a negative air pressure may be defined as any pressure lower than 760 mmHg.

Optionally, the air pump 103 may also be configured to generate a positive air pressure in the nipple tunnel 109. For example, a positive air pressure may be used to assist with emptying or evacuating of elements of the breast pump 100. In particular, a positive air pressure can be used to expel milk from the milk bottle 104.

The air pump 103 may be a rotary diaphragm pump. A rotary diaphragm pump is a positive displacement pump that uses a combination of the reciprocating action of a flexible diaphragm (e.g. made from silicone, rubber, or thermoplastic) and suitable valves on either side of the diaphragm to pump a fluid. In the case of some embodiments of the present invention the rotary diaphragm pump pumps air. A rotary air pump provides a cost effective and easy way to reach desired pressures. In this case, the air pumping subsystem may either be configured as an open loop or closed loop pumping subsystem. The rotary diaphragm pump used may be a standard rotary diaphragm pump as is known for use in breast pump 100.

Alternatively, the air pump 103 may be a piezoelectric pump. Piezoelectric air pumps (or piezo pumps), operate silently (e.g. outside the range of human hearing) and with minimal vibrations. Due to their low noise, strength and compact size, piezoelectric pumps are ideally suited to the embodiment of a small, wearable breast pump. However, piezo pumps generate higher heat as compared to, for example, rotary diaphragm pumps. Reducing the air volume in the system improves the efficiency of the pump, and the pump therefore generates less heat. When a piezoelectric pump is used, the air pumping subsystem may also either be configured as an open loop or closed loop pumping subsystem.

Other possible types of pumps may also be feasibly usable in embodiments of the present invention. For example, a peristaltic or vein pump could also be used.

In an embodiment the pump is housed within the in-bra breast pump 100. However, the pump may optionally be housed separately and connected to the in-bra architecture by simple tubing.

The wearable breast pump 100 may be configured to operate quietly in normal use. A cavity containing the air pumping subsystem (comprising the air pump 103 and solenoid valve 105), may be sealed and comprise other noise reduction technology so as to further attenuate sound.

The air pump 103 may be configured to pump at a wide range of different levels of intensity. A first level of pumping is provided to generate the base level vacuum inside the nipple tunnel 109. A second level of pumping is provided to generate a pumping vacuum to stimulate the breast tissue and initiate milk expression from the breast. The second level of pumping is more intense than the first level. This is because a greater negative air pressure must be generated for when the air pump 103 is expressing milk from the user's breast 102, compared to when only the base level vacuum desired pressure is required.

The first level of pumping is configured to produce a negative air pressure of from −15 to −70 mmHg (relative to atmospheric pressure) inside the nipple tunnel 109. In an embodiment, the first level of pumping is configured to produce a negative air pressure of from −30 to −60 mmHg (relative to atmospheric pressure) inside the nipple tunnel 109. In an embodiment, the first level of pumping is configured to produce a negative air pressure of −50 mmHg (relative to atmospheric pressure), plus or minus 10%, inside the nipple tunnel 109. The above pumping pressures are disclosed as merely examples, and the skilled person would understand that other feasible ranges are possible. The first level of pumping may also be determined by a user's preferences and input via a connected device to the breast pump.

The second level of pumping is configured to produce a negative air pressure of from −10 to −300 mmHg (relative to atmospheric pressure) inside the nipple tunnel 109. In an embodiment, the second level of pumping is configured to produce a negative air pressure of from −25 to −280 mmHg (relative to atmospheric pressure) inside the nipple tunnel 109. In an embodiment, the second level of pumping is configured to produce a negative air pressure of from −50 to −280 mmHg (relative to atmospheric pressure) inside the nipple tunnel 109. The above pumping pressures are disclosed as merely examples, and the skilled person would understand that other feasible ranges are possible. The second level of pumping may also be determined by a user's preferences and input via a connected device to the breast pump.

Breast Shield

The breast shield 101 may comprise a second diaphragm 112, the function of which will be explained below in more detail. The second diaphragm 112 may comprise a breast flange 108 for fitting to the user's breast 102 and a nipple tunnel 109 for receiving a nipple. The breast flange 108 contacts the user's breast 102 and seals the breast shield 101 to the surface of the user's breast 102. The breast flange 108 may be a funnel or conical shape that is well adapted to receive a human breast. The nipple tunnel 109 is a tubular shape extending from the breast flange 108 and may be integrally formed with the breast flange 108. The nipple tunnel 109 may also feasibly be other shapes such as a cuboid, triangular or cylinder. It is desirable to reduce excess air volume in the system to enable performance gains in the cycle rate of the pump, therefore increasing the efficacy of milk production, pump performance and battery performance.

The breast shield 101 is, optionally, designed to be flexible so that it may collapse and expand when exposed to different pressures generated by the air pump 103. When in a collapsed state, the minimum volume of air is present internally inside the nipple tunnel 109 of the breast shield 101. By ensuring the nipple tunnel 109 sits as close to/moulds to the nipple/breast as possible, it also fits to any size of nipple and supports the areola from being pulled into the breast shield. The air pump 103 actuates on the external walls of the nipple tunnel 109 causing it to dilate radially around a central axis through the nipple tunnel 109. The initial dilation and relaxation causes the nipple tunnel 109 to conform to the shape of the nipple, thereby reducing excess air volume in the system. The dilation of the nipple tunnel 109 can be caused by folding of the material of the nipple tunnel 109 or by the elasticity of material the nipple tunnel 109 is made from (e.g. silicone).

When the air pump 103 is actuated, fluid (i.e. air and/or milk) is removed from inside the breast shield 101 and nipple tunnel 109. This causes the breast shield 101 to move closer to the nipple of the user, which reduces the amount of air inside the nipple tunnel 109 and maximises the volume of a chamber on the dry side of the breast shield 101. This ensures the desired peak pressure can be reached without the pump 103 reaching its maximum operating range.

Figure 1A:
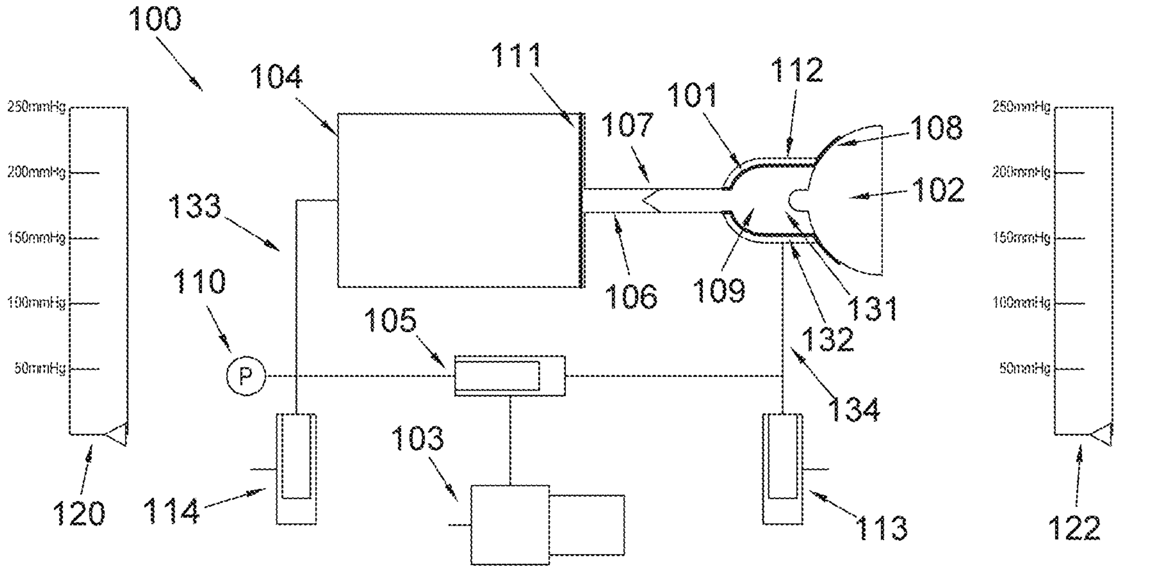
FIG. 1*a* shows a breast pump where the breast pump is being fitted to the user's breast according to an embodiment of the invention.
Figure 1B:
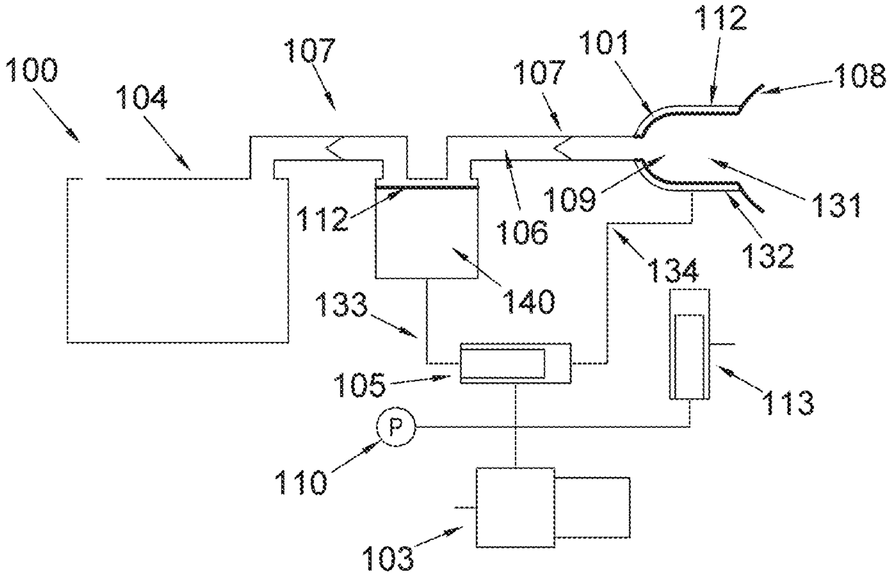
FIG. 1*b* shows a breast pump where the breast pump is being fitted to the user's breast according to an embodiment of the invention comprising an antechamber.

The breast shield 101 may comprise a first side 131 and a second side 132 (as labelled in FIGS. 1*a* and 1*b*). The first side 131 of the breast shield 101 is the internal side and faces the user's breast when in use. The first side 131 of the breast shield 101 is configured to receive the user's breast. The second side 132 of the breast shield 101 is the external side and faces away from the user's breast when in use. The first side 131 of the breast shield 101 is configured to be in contact with milk expelled from the user's breast, whereas the second side 132 of the breast shield 101 is not generally configured to be in contact with expressed milk (except in the case of misuse and leaks). The second side 132 of the breast shield may comprise a frame to allow the breast shield 101 to be fitted to and removed from the breast pump 100. The frame may be rigid such that it supports the flexible breast shield 101. The second side 132 is configured to latch onto the breast pump 100 when in use. The frame may be configured to be removably attached to the breast pump 100 using one or more spring plungers which hold the frame in place when attached. The frame may comprise one or more locating grooves to provide alignment with, and therefore easy attachment to, the breast pump 100.

Because the shape or configuration of the nipple tunnel is dynamic, the shape of the nipple tunnel is able to always be as big as it only needs to be, therefore reducing the air volume. Advantageously, the opening of the nipple tunnel at the interface with the breast can be increased by expanding the second diaphragm 112 when placing the nipple inside the nipple tunnel, and once the nipple is correctly placed inside the nipple tunnel, the second diaphragm 112 can be used to collapse the opening at the interface with the breast to the desired size around the breast or nipple area.

The parameters of the breast shield are configured to enhance the overall performance and user experience. Parameters including material choice, hardness, overall geometry or size, thickness may be varied.

Channels

The breast pump 100 may also comprise first 133 and second channels 134. The first channel 133 draws the base level vacuum on a first side 131 of the breast shield 101, applying a negative pressure to the inner walls of the nipple tunnel 109. The second channel 134 draws the pumping vacuum on a second side 132 of the breast shield 101, applying a negative pressure to the outer walls of the nipple tunnel.

The first channel 133 comprises, at least in part, a longitudinal path for receiving breast milk from the breast shield. The first channel 133 connects the air pump 103 to the first side 131 of the breast shield 101. The first channel 133 may also pass through the milk bottle 104. A bottle bleed solenoid 114 may be attached to the first channel 133. The first channel 133 extends to an internal portion of the breast shield 101 (i.e. the internal side which faces the user's breast when the pump is in user). The first channel 133 may extend to the first side 131 of the breast shield 101. The first channel 133 may extend into the nipple tunnel 109 of the breast shield 101.

The second channel 134 connects the air pump 103 to the second side, outer side, 132 of the breast shield 101. The second channel 134 may comprise a path extending outwardly from the breast shield 101. The second channel may comprise a radial path an angle to the longitudinal path.

The radial path may be at 90 degrees or less to the longitudinal path. The radial path may be perpendicular to the longitudinal path for receiving breast milk from the breast shield. The orientation of the radial path with respect to the longitudinal path may change depending on the connection of the breast shield 101 to the pump 103. The second channel 134 does not pass through the milk bottle 104. A breast shield solenoid 113 may be attached to the second channel 134.

The first 133 and second channels 134 may be independently controlled and are not connected to one-another. This allows a breast pump system to be generated which has an air pump 103 which alternately switches between delivering a base level vacuum and a pumping vacuum. The first channel 133 delivers the base level vacuum via the air pump 103 and the second channel 134 delivers the pumping vacuum via the same air pump 103. Applying the pumping vacuum to the external side of the breast shield (i.e. the external walls of the nipple tunnel) can cause radial expansion of the nipple tunnel, which mimics suction by a child's mouth.

The breast pump switches between delivering the base level vacuum and the pumping vacuum according to the users' requirements and pumping profiles. Two channels are required to deliver the base level vacuum independently from the pumping vacuum. In generic breast pumps when the pumping vacuum is turned off, the air pressure returns to atmospheric pressure, whereas, the breast pump disclosed herein allows for the constant low level base level vacuum to be maintained.

The base level vacuum system with two channels also reduces the likelihood of milk leaking from the breast pump during use. The base level vacuum ensures constant suction of the breast shield to the nipple and breast, meaning that contact is maintained even when the standard pumping vacuum is not being applied. This constant suction also allows the user to pump whilst bending or lying down since the breast shield is fixed to the user's breast.

The use of one pump on both channels results in an efficient, small and compact breast pump that can be readily worn discreetly in bra.

Diaphragms

In one embodiment, to achieve the base level vacuum system, two diaphragms are needed. The first diaphragm 111 operates the base level vacuum and the second diaphragm 112 works to express breast milk from the user's breast 102. The first 111 and second 112 diaphragm are made from flexible materials and are designed to deform when a negative air pressure is drawn by the air pump 103.

The breast pump 100 is a closed loop system, preventing any fluids (i.e. milk or air) from entering or exiting the system. The first diaphragm 111 and second diaphragm 112 close the system by preventing fluids from entering or exiting the base level vacuum once it has been generated. This acts as a back-flow prevention mechanism and also allows the base level vacuum to be consistently maintained (until the system changes, for example by the introduction of expressed breast milk and then the base level vacuum can be 'topped up'). A closed loop system provides the additional benefit of providing a breast pump 100, more suitable for sterilization, since milk cannot travel to areas of the breast pump 100 it should not, such as the air pump 103, for example.

Two diaphragms are shown in FIGS. 1 to 13. In one embodiment, the first diaphragm 111 is comprised within the housing of the breast pump 100. Optionally, the first diaphragm 111 may not be visible to the user when the breast pump 100 is in use. Accordingly, the first diaphragm 111 may be entirely comprised within the housing of the breast pump 100.

Figure 14:
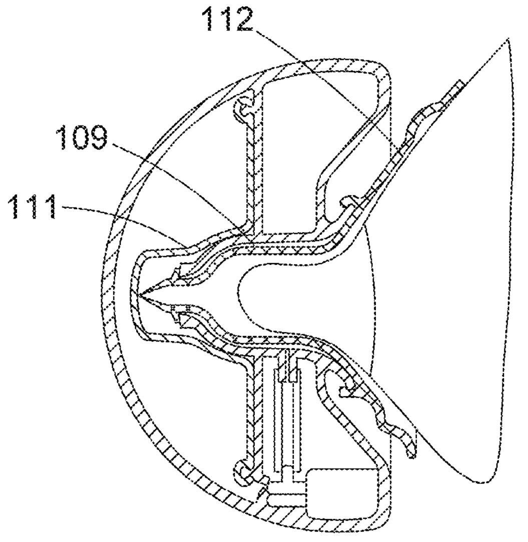
FIG. 14 shows a breast pump according to an embodiment of the invention.

An example configuration of the two diaphragms is provided in FIG. 14. The wearable breast pump system in FIG. 14 comprises a first flexible diaphragm 111, and a second flexible diaphragm 112.

The nipple tunnel 109 forms part of the second diaphragm 112 (i.e. the breast shield). When a nipple is placed inside the nipple tunnel 109, and air is pumped from the nipple tunnel via the first path to reach and maintain a base level vacuum, the second diaphragm 112 is configured to expand or contract radially such that nipple tunnel and breast shield moulds onto the breast and nipple. This step creates a better fit around the breast and nipple area and removes redundant air out of the nipple tunnel further improving the overall performance of the system using the second diaphragm 112. The second diaphragm 112 is repeatedly 'topped up' through the pumping session to maintain this base level vacuum as the pressure in the closed system decays (for example when milk and or air enters the milk bottle 104). When the base level vacuum is generated or 'topped up' the nipple tunnel 109 contracts, reducing any redundant air inside the second diaphragm 112 (i.e. the breast shield 101 and the nipple tunnel 109).

When the pump is actuated, the second diaphragm 112 is configured to expand or contract radially, which in turn causes the nipple to be stimulated and/or to be drawn into the nipple tunnel 109.

In one embodiment, the first diaphragm 111 may be located inside the milk container 104.

The first diaphragm 111 is designed to draw a base level vacuum inside the nipple tunnel by pulling air laterally outwards away from the user's breast and along the axis of the user's nipple. In contrast to this a pumping vacuum is pulled radially around the central axis of the user's nipple when a vacuum is drawn through channel 133, air is removed from the inside of the first diaphragm.

Optionally, each of the first diaphragm 111 and second diaphragm 112 may be connected to a pressure sensor (not shown) to monitor the pressure held by each diaphragm. These pressure sensors may be used, for example, to calculate how much air has been removed from the system and/or may also aid with measuring milk flow into the milk container 104.

In an alternative embodiment, as shown in FIG. 1*b*, the first diaphragm 111 may be located inside the housing of the breast pump 100 but not within the milk container 104. Instead, the first diaphragm 111 may be located in a separate antechamber 140 intermediate to the second diaphragm 112 and the milk container 104 or intermediate to the milk container 104 and the air pump 103. The first diaphragm 111 may be located between the non-return valve 107 and the milk container 104.

Milk Container

The wearable breast pump 100 system may comprise a milk container 104 that is configured to prevent any milk leaks from the milk container 104. The milk container 104 provides a hermetic seal to both the air pump 103 and the breast shield 101 so that a vacuum can be drawn inside the bottle without any air leaks. Similarly, the hermetic seal prevents any milk from leaking out of the bottle. The milk container 104 is designed to receive the breast milk from the nipple tunnel 109 and store the breast milk whilst the user continues to operate the breast pump 100. The milk container 104 can be a re-useable milk container that is connected to the housing. The milk container has an external surface shaped to continue a curved or breast-like shape of the pump.

The milk container 104 may be a flexible bottle with a rigid exoskeleton. The milk container 104 may also be a rigid bottle with a flexible interior portion.

In an alternative configuration, the milk container 104 may be a milk bag. In this configuration the milk bag may be single-use or multi-use. The milk bag may be configured to fit within a milk bag housing to support the milk bag when collecting milk.

Non-Return Valve

A non-return valve 107 may be provided at the downstream end of the nipple tunnel 109. The non-return valve may act to reduce the volume of air to be worked by the pump. The non-return valve 107 is designed to allow fluid to pass in only one direction. Therefore, in some embodiments of the present invention breast milk is allowed to pass from the nipple tunnel 109 of the breast shield 101 to the milk container 104 where it is stored. The air pump 103 draws milk or air from the nipple tunnel 109 of the breast shield 101 to the milk container 104 and it is allowed to flow past the non-return valve 107. The valve is designed in shape so that when fluid (i.e. milk or air) enters the valve its pressure holds the closing mechanism open. However, milk or air flow from the milk container 104 to the nipple tunnel 109 of the breast shield 101 is blocked due to the pressure of the milk or air on the non-return valve 107. The valve is designed so that if the fluid attempts to flow back through the non-return valve 107 in the wrong direction, the closing member is forced back over the entrance of the non-return valve 107 preventing any flow. This ensures that when base level vacuum is not applied, no fluid leaks from the milk container 104 back into the nipple tunnel 109 and towards the user.

The non-return valve 107 is located either at or intermediate to the exit of the nipple tunnel 109 and/or the entrance to the milk container 104. In an embodiment, the non-return valve 107 is located at the entrance of the milk container 104 to avoid any milk leaking out of the milk container 104 and into the tube 106. The breast pump 100 may also comprise at least one support means or tube 106 arranged internally to receive and hold the non-return valve 107. The non-return valve may be flexible.

In one embodiment, the non-return valve 107 may be an umbrella valve. Umbrella valves are elastomeric valve components that have a diaphragm shaped sealing disk (i.e. an umbrella shape). When mounted in position, such as in the tube 106, the convex diaphragm flattens out against the valve seat and absorbs a certain amount of seat irregularities and creates a sealing force. The main advantage of an umbrella valve is that they can be preloaded with a closing force so when the milk container 104 is removed away from the vacuum source (for example, at the end of the pumping session), it remains shut under atmospheric pressure. This provides the advantage of preventing milk leakage when transporting and storing collected milk.

In an alternative embodiment, a duck bill valve may be used as a non-return valve 107. Duckbill valves are one-piece, elastomeric components that act as backflow prevention devices or one-way valves. They have elastomeric lips in the shape of a duckbill which prevent backflow and allow forward flow. The main advantage of duckbill valves over other types of one-way valves is that duckbill valves are self-contained i.e. the critical sealing function is an integral part of the one piece elastomeric component as opposed to valves where a sealing element has to engage with a smooth seat surface to form a seal. When a duck bill valve is used as a non-return valve 107, the duck bill valve will generally be at least partially open under atmospheric pressure, making leaks more likely when a vacuum is not applied to the system or during transportation or storage of the milk container 104.

In an alternative embodiment, a flap valve may be used as a non-return valve 107. A flap valve ensures that fluid can pass through the valve in one direction only as the pressure of the fluid pushes the swinging door open. When the pressure differential drops below a certain point, the flap closes. In any embodiment of non-return valve 107 as described herein, the non-return valve may self-seal, e.g. close, under negative pressure against an opening to the milk container 104. The opening to the milk container 104 may be located in the nipple tunnel 109. The negative pressure against the opening may be considered to be a pressure differential across the non-return valve 107, e.g. a pressure differential across the opening to the milk container 104. The pressure differential may be an air pressure differential, e.g. a negative air pressure differential.

Switching Means

It may be advantageous to the user to make an in-bra wearable breast pump as small and compact so that it is as discreet as possible, and it may not be noticeable that they are wearing and operating a breast pump. This may be achieved by using one pump to operate both diaphragms 111, 112. The breast pump 100 comprises a switching means to switch the breast pump between a first mode and a second mode to operate the first 111 and second 112 diaphragms respectively. The switching means controls the application of vacuum to each diaphragm. In the first mode, the switching means ensures that the air pump acts on the first diaphragm 111 to generate the base level vacuum. In the second mode, the switching means ensures that the air pump acts on the second diaphragm 112 to generate the pumping vacuum.

The switching means may comprise a three-way solenoid valve, as described below. Alternatively, the switching means may comprise two two-way solenoid valves. Alternative switching means are also feasible within the realms of what would be considered by a person skilled in the art.

Embodiments of the present invention may be described with reference to either a generic switching means, a three-way solenoid valve or two solenoid valves in parallel or any of conceivable switching means. Alternatively, to avoid needing to switch between two modes on the same air pump 103, two separate air pumps 103 could be used to generate each of the first and second levels of pumping. For the purposes of some embodiments of the invention, these elements may be interchangeable and may be swapped to achieve the same effects.

Three-Way Solenoid Valve

A three-way solenoid valve 105 may be provided as part of the breast pump 100. The three-way solenoid valve 105 is a valve. The three-way solenoid valve 105 comprises two modes. In the first mode, the three-way solenoid valve 105 is configured to allow air to flow from the first diaphragm 111 to the air pump 103. In the second mode, the three-way solenoid valve 105 is configured to allow air to flow directly from the second diaphragm 112 to the air pump 103. Directly means that the air does not flow via the milk container 104.

Figure 15A:
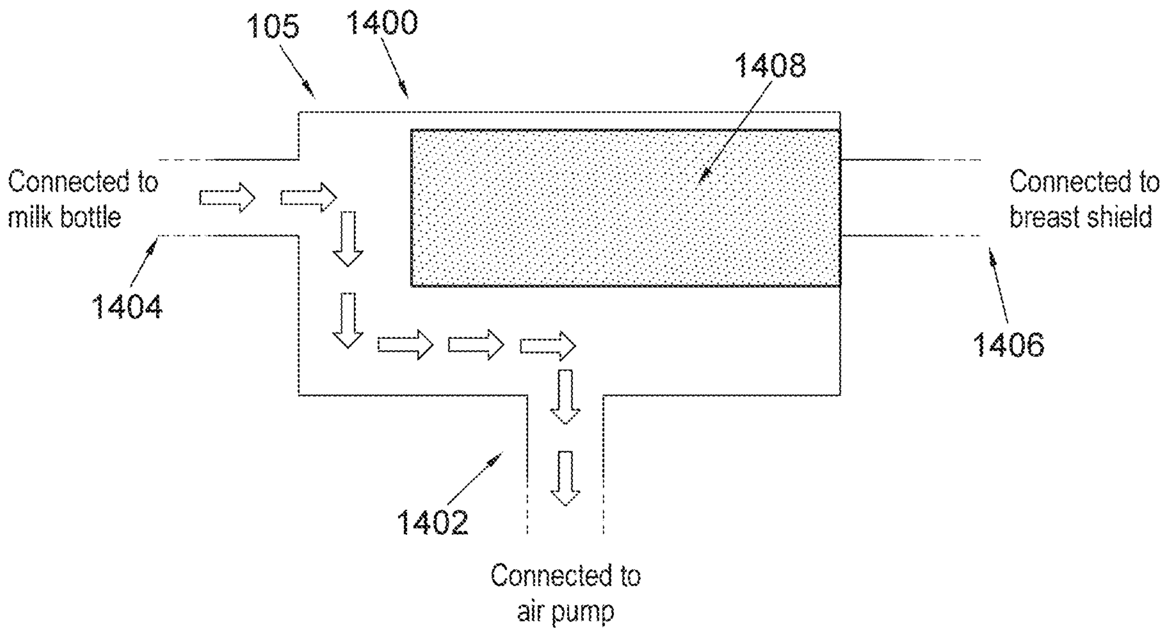
FIGS. 15*a* and 15*b* show an example of a three way solenoid valve according to an embodiment of the invention.
Figure 15B:
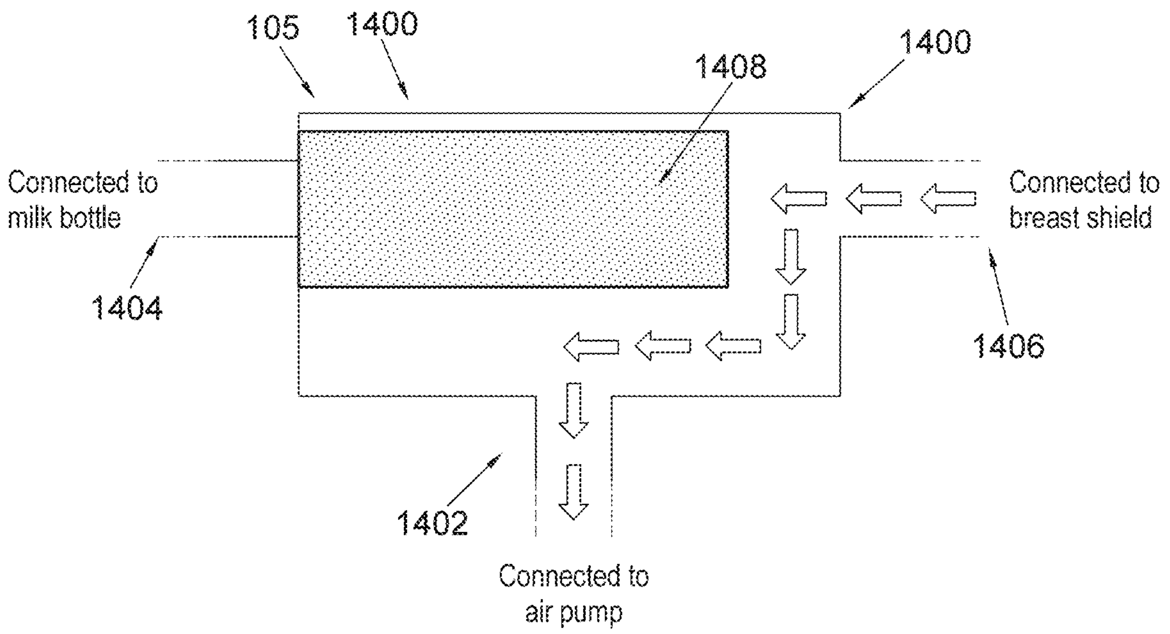

An embodiment of the three-way solenoid valve 105 is shown in FIGS. 15*a* and 15*b*. As shown in FIGS. 15*a* and 15*b*, the three-way solenoid valve 105 comprises a housing structure 1400 with three ports. The housing structure 1400 provides a passage of air between the ports of the solenoid. A first port 1402 is connected to the air pump 103, a second port 1404 is connected to the milk container 104 and the third port 1406 is connected to the breast shield 101. The three-way solenoid valve 105 also comprises a movable block 1408 which is configured to move between two positions.

The three-way solenoid valve 105 switches between a first position (FIG. 15*a*) and a second position (FIG. 15*b*). As shown in FIG. 15*a*, in the first position (i.e. the first mode) the three-way solenoid valve 105 is configured to allow air to flow from the milk container 104 to the air pump 103. In other words, air is allowed to flow from the first port 1402 to the second port 1404. The air pump 103 can be configured to draw air outwards from the milk container 104 (and by extension from the breast shield 101 and nipple tunnel 109). This generates a negative air pressure in the milk container 104 and nipple tunnel 109. In the first position the movable block 1408 of the three-way solenoid valve 105 is configured to block the third port 1406, as shown in FIG. 15*a*. This prevents air from flowing directly between the air pump 103 and the breast shield 101, however, allows air to flow between the air pump 103 and the milk container 104.

As shown in FIG. 15*b*, in the second position (i.e. the second mode) the three-way solenoid valve 105 is configured to allow air to flow directly from the breast shield 101 to the air pump 103. Specifically, in the second position the three-way solenoid valve 105 is configured to allow air to flow directly from the nipple tunnel 109 to the air pump 103. In other words, air is allowed to flow directly from the first port 1402 to the third port 1406. The air pump 103 can be configured to draw air outwards from the breast shield 101 and nipple tunnel 109 directly. This generates a negative air pressure in the breast shield 101 and nipple tunnel 109, however, there is no impact on the air pressure in the milk container 104. In the second position the movable block 1408 of the three-way solenoid valve 105 is configured to block the second port 1404, as shown in FIG. 15*b*. This prevents air from flowing directly between the air pump 103 and milk container 104, however, allows air to flow between the air pump 103 and breast shield 101 (and nipple tunnel 109).

The three-way solenoid valve 105 may also feasibly have a neutral mode, where it is in neither of the first or second modes and allows air to flow freely between each port.

The three-way solenoid valve 105 is added to the system to draw a vacuum directly on to the nipple or breast tissue (away from any milk ducts) so that in a first mode the air pump can provide a constant low level vacuum to secure the unit to the user and in a second mode the air pump can provide a pumping vacuum to the user's breast. This architecture provides no leaks at the breast interface, holds the pump in position and is designed to feel re-assuring to the user.

As an alternative to using a three-way solenoid valve, two separate valves may be employed to achieve the same effect. Such valves may be solenoid valves or any other valve that is within the realms of what would be considered by a person skilled in the art.

Figure 15C:
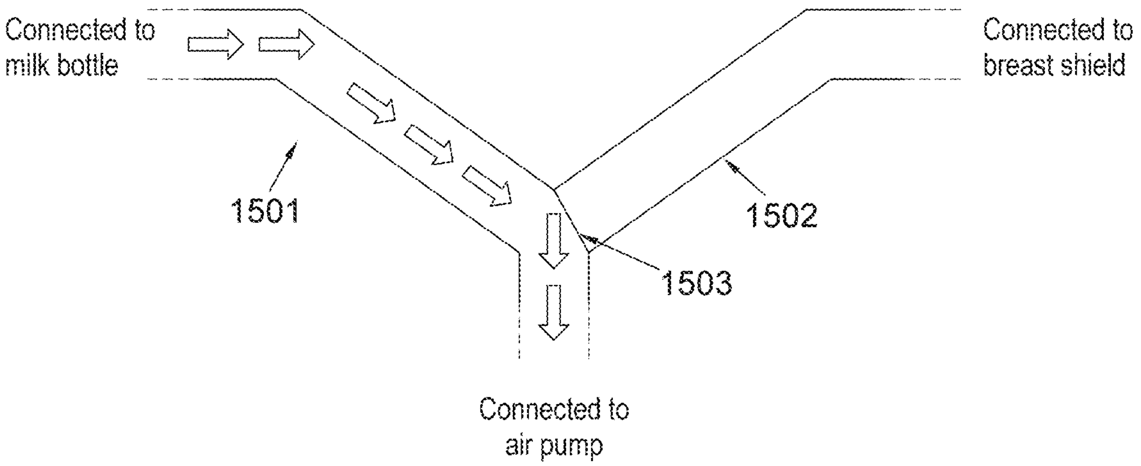
FIGS. 15*c* and 15*d* show an example of a generic switching means according to an embodiment of the invention.
Figure 15D:
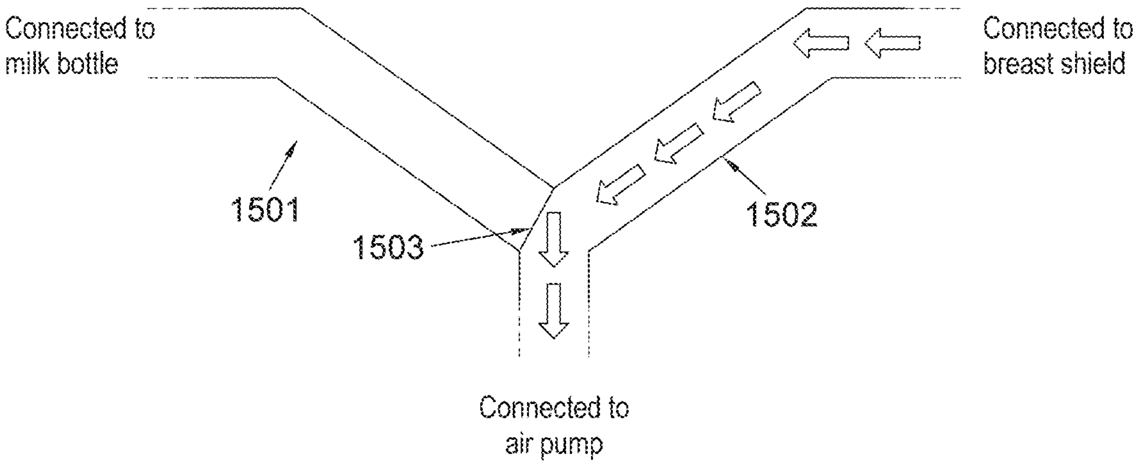

If two separate valves are provided as part of the breast pump 100, when they are connected in parallel they comprise two modes. In the first mode, a first valve 1503 is configured to allow air to flow from the milk container 104 to the air pump 103 (as shown in FIG. 15*c*). In the second mode, a second valve 1504 is configured to allow air to flow directly from the nipple tunnel 109 to the air pump 103 (as shown in FIG. 15*d*). Directly means that the air does not flow via the milk container 104.

Pressure Sensor

Optionally, a pressure sensor 110 may be provided in the system. The pressure sensor 110 may be provided between the air pump 103 and the milk container 104. A second pressure sensor may be provided between the air pump 103 and the breast shield 101 (not shown).

The pressure sensors 110 can be used to actively monitor the first diaphragm 111 to ensure a consistent base level vacuum throughout the system. In some embodiments the breast pump 100 may comprise one or more additional pressure sensors configured to measure the pressure at the second diaphragm 112.

The pressure sensor 110 may be used to assist in the measurement of milk collection in the milk container 104, by calculating pressure changes in the milk container 104.

Base Level Vacuum Bleed Valve

Optionally, a base level vacuum bleed valve 114 may be provided. The base level vacuum bleed valve is connected to the first diaphragm 111 and the air pump 103. The base level vacuum bleed valve 114 may be a solenoid valve which has two ports. Alternative valves are also feasible within the realms of what would be considered by a person skilled in the art.

The base level vacuum bleed valve 114 is provided to allow the first diaphragm 111 to return back to atmospheric pressure such as when measuring the volume of milk in the milk container or if the user wants to remove the breast pump 100. The base level vacuum bleed valve 114 allows a vacuum to be pumped from the first diaphragm 111 when the valve is 'closed'. When it is necessary to remove the pump or take a milk volume measurement, it is necessary to return to atmospheric pressure. This is achieved by turning the pump off and opening the base level vacuum bleed valve 114 which in turn allows air to rush back into the pump, re-pressurising it to atmospheric pressure.

In an embodiment, the base level vacuum bleed valve 114 is provided to allow the milk container 104 to return back to atmospheric pressure such as when the user wants to remove the breast pump or alternatively remove the milk container 104 from the breast pump 100.

The bottle bleed solenoid 114 also functions to allow an accurate milk volume measurement to be taken throughout the cycle, since it is required to reduce the pressure in the milk container 104 to atmospheric pressure to obtain an accurate measurement of the milk volume collected in the milk container 104.

Breast Shield Bleed Valve

The second diaphragm 112 may be connected to a breast shield bleed valve 113, that is configured to reset the air pressure in the nipple tunnel to a base level vacuum when the air pump stops and ensure the breast pump 100 remains firmly attached to the user's breast 102. The breast shield bleed valve 113 is connected to the second diaphragm 112 and the air pump 103. The breast shield bleed valve 113 may be a solenoid valve which has two ports. Alternative valves are also feasible within the realms of what would be considered by a person skilled in the art.

The breast shield bleed valve 113 may be a two-way solenoid valve which has two ports. The breast shield bleed valve 113 allows a vacuum to be pumped when the two-way solenoid valve is 'closed' and then when the user wants to return to base level vacuum pressure, the user can turn the pump off and 'open' the solenoid which in turn allows air to rush back into the pump, re-pressurizing it. The breast shield bleed valve 113 is configured to open to release the pumping vacuum from the breast shield 101/second diaphragm 112. This allows air pressure in the nipple tunnel 109 and surrounding the first diaphragm 111 to return to the base level vacuum level rather than the pumping level. Using this configuration, the air pump 103 can remain on at all times, as the effect of the air pump 103 is neutralized by opening the breast shield bleed valve 113.

Air Pumping and Base Level Vacuum System

FIGS. 1 to 13 show the process of how the base level vacuum is generated and maintained throughout a pumping cycle and whole pumping sessions in some embodiments. As described herein, the process may be characterized by the switching of the three-way solenoid valve between the first and second modes. Alternatively, as the skilled person would understand the process may instead be carried out by using two valves in parallel, an alternative switching means or by using two separate air pumps 103. The process is described with reference to the three-way solenoid valve for ease only.

Figure 16:
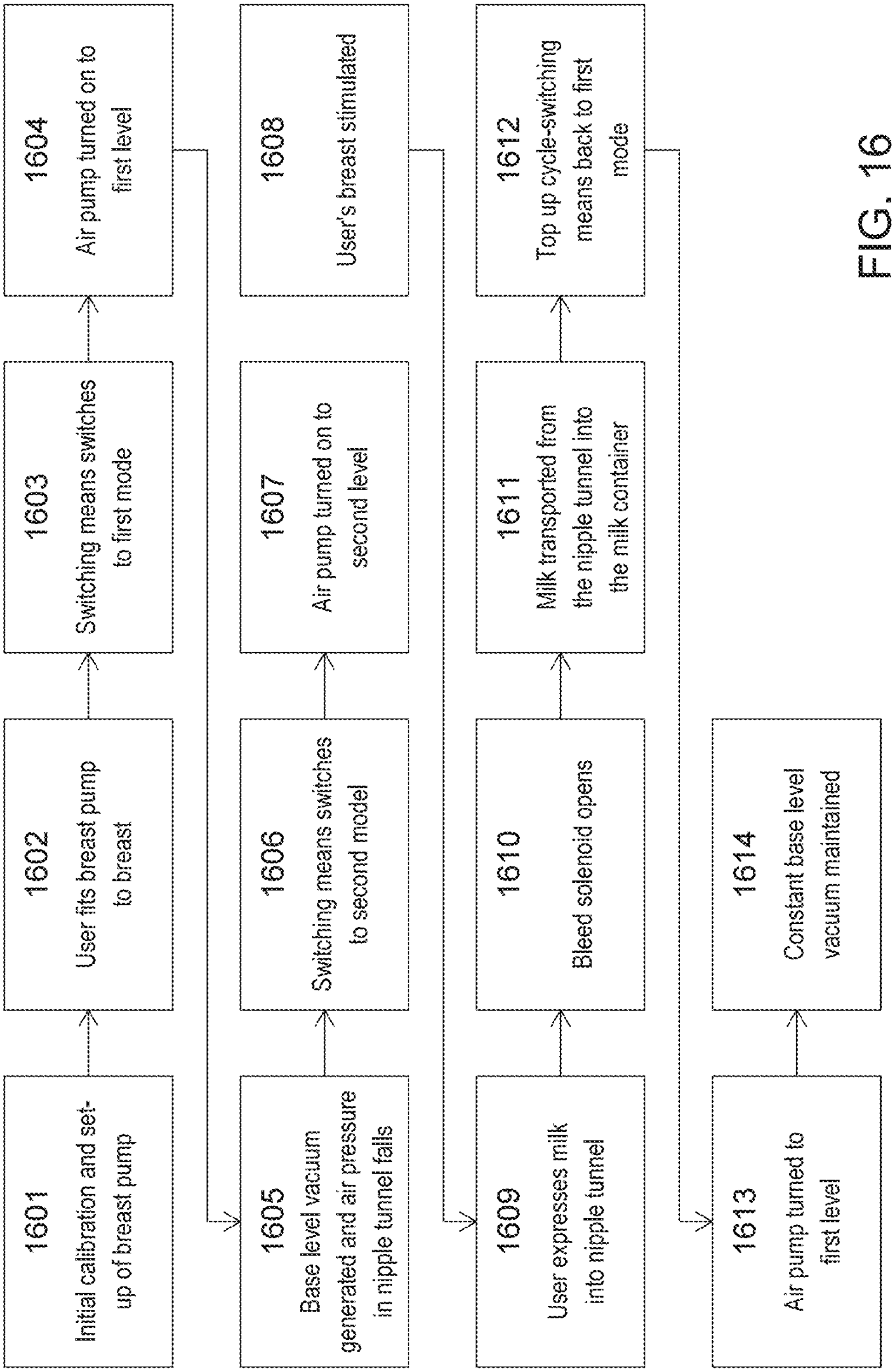
FIG. 16 shows the method of operation of the breast pump according to an embodiment of the invention.

Additionally, FIG. 16 shows the process steps followed to generate and maintain the base level vacuum during a pumping session.

As a first step, the initial setup of the breast pump system takes place (step 1601). The initial setup of the breast pump system may comprise calibration of the milk container 104, calibration and resetting of any pressure sensors 110 in the system and a start-up cycle to set up the air pump 103. At this time the three-way solenoid valve 105 may be positioned in either the first or second mode or in a neutral mode to allow calibration of the breast pump 100 system to take place. Haptics and visual indicators may be used to confirm that the breast pump is properly assembled and ready to start stimulation mode.

The air pressure inside the milk container 104 is shown by a first scale 120 on the left hand side of FIGS. 1 to 13. The pressure inside the nipple tunnel 109 is shown by a second scale 122 on the right hand side of FIGS. 1 to 13. During the calibration and set up period, the air pressure inside the milk container 104 and nipple tunnel 109 is equivalent to the surrounding ambient air pressure (also known as atmospheric pressure). A controller, 1800 (not shown in FIGS. 1-13), takes a measurement of the ambient air pressure, in order to calculate a desired base level vacuum pressure.

When the start-up and calibration of the breast pump 100 is complete, the breast pump 100 is fitted to the user's breast 102 (step 1602), as shown in FIG. 1. The user initiates the pumping process by applying the breast shield 101 and fitting the breast shield 101 comfortably to the surface of the breast. The breast shield 101 can be applied by inserting the nipple into the entrance of the relaxed nipple tunnel 109. Then a low level pump vacuum may be applied (not shown in FIGS. 1 to 13) to draw the nipple fully into the nipple tunnel 109 and to achieve a base level vacuum. Alternatively, the user can apply pump vacuum to open the nipple tunnel 109 and then subsequently place their nipple into the opening and then relax the flexible nipple tunnel 109 before drawing a base level vacuum to close, and ultimately seal the flexible breast shield 101 to the user's nipple.

In some embodiments, throughout the whole pumping process, only a single air pump 103 is required. This air pump 103 is used to both maintain the base level vacuum and to generate the pumping vacuum. The three-way solenoid 105 (or alternative switching means) is used to switch between the base level vacuum and the pumping vacuum.

Feasibly, the initial calibration (step 1601) could take place after the user fits the breast pump to the breast (step 1602).

Figure 2:
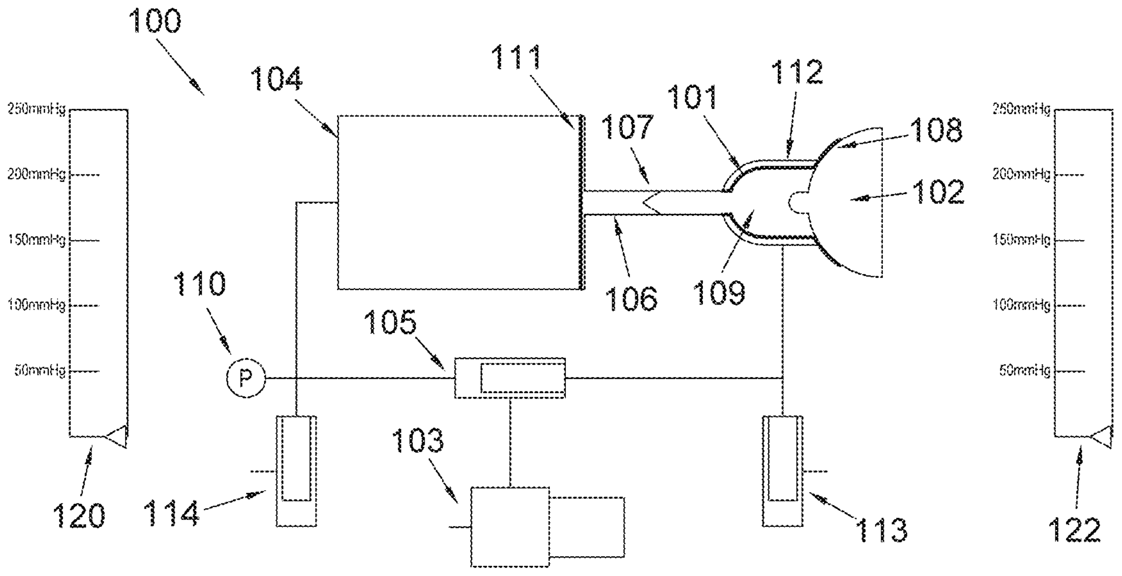
FIG. 2 shows a breast pump with a three-way solenoid valve switching settings according to an embodiment of the invention.

Once the breast pump has been fitted to the user's breast, the three-way solenoid valve 105 switches into the first mode (step 1603). FIG. 2 shows a breast pump 100 with a three-way solenoid valve 105 in the first mode. A specific example of a three-way solenoid valve 105 in the first mode is shown in FIG. 15*a*. In the first mode, the three-way solenoid valve 105 is configured to allow air to flow from the milk container 104 to the air pump 103. During this switching process, the air pressure inside the milk container 104 and nipple tunnel 109 remain equivalent to the surrounding air pressure.

The three-way solenoid valve 105 controls the application of vacuum to each diaphragm. In the first mode, the three-way solenoid valve 105 ensures that the air pump 103 acts on the first diaphragm 111 to generate the base level vacuum. In the second mode, the three-way solenoid valve 105 ensures that the air pump 103 acts on the second diaphragm 112 to generate the pumping vacuum.

Figure 3:
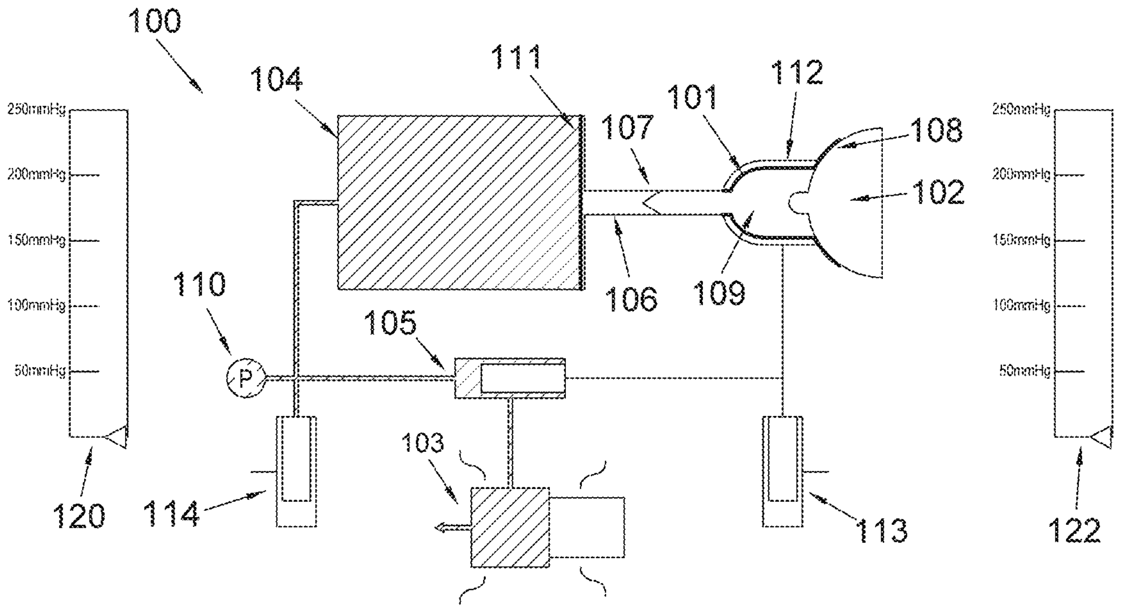
FIG. 3 shows a breast pump where an air pump of the breast pump is turned on according to an embodiment of the invention.

Next, as shown in FIG. 3, the air pump 103 is turned on to the first level (step 1604). When the air pump 103 is turned on, air is evacuated from the first channel 133. As a consequence of air being evacuated from the pump side of the milk container 104, air is also evacuated from the nipple tunnel 109 of the breast shield 101 during this process. A negative air pressure is generated in the milk container 104. The negative air pressure inside the milk container 104 causes a pulling force on the first diaphragm 111 positioned inside the milk container 104. The air is evacuated from the nipple tunnel 109 by the pulling force of the first diaphragm 111. This pulling force generates a low-level base level vacuum inside the nipple tunnel 109 (step 1605). Application of the vacuum to the first diaphragm 111 causes negative pressure in the milk container 104 which draws fluid (air or milk) from the nipple tunnel to the milk container 104. This is used to achieve the base level vacuum in the system and ensures a secure fit of the breast shield 101 to the breast. The base level vacuum provides the benefit of increase biomimetic motion, to mimic the constant suction maintained by a baby whilst breastfeeding.

The base level vacuum is held inside the nipple tunnel 109 (i.e. on the side facing the user's breast). The base level vacuum will be held on both sides of the first diaphragm 111. Occasionally, the base level vacuum will be released in the milk container 104 by opening a bottle bleed solenoid 114 (e.g. when milk flows into the milk container 104 or if it is required to take a milk measurement). When the pressure is released to atmospheric pressure in the milk container 104, the base level vacuum will be maintained in the nipple tunnel 109 because the non-return valve 107 will close due to a pressure differential and prevent any fluid escaping from the nipple tunnel 109.

The non-return valve 107 allows fluid to be pulled from the nipple tunnel 109 into the milk container 104 to generate and maintain the base level vacuum even when the milk bottle is being depressurized. Once this fluid has passed through the non-return valve 107 it is not possible for it to flow back in the opposite direction (i.e. back towards the nipple tunnel 109). Therefore, this fluid is permanently extracted from the nipple tunnel 109. Fluid is permanently extracted until such time as the breast shield 101 is removed from the user's breast 101. Since there is a seal around the user's breast 102, air cannot enter the system through the opening of the breast shield 101. The non-return valve 107 ensures fluid cannot enter the breast shield 101 via the opening to the milk bottle 104. Therefore, fluid is permanently extracted from the nipple tunnel 109 until an action is taken to reintroduce air or fluid to the system. In the absence of an action taken to reintroduce air or fluid, the nipple tunnel 109 will remain at the base level vacuum pressure.

Figure 4:
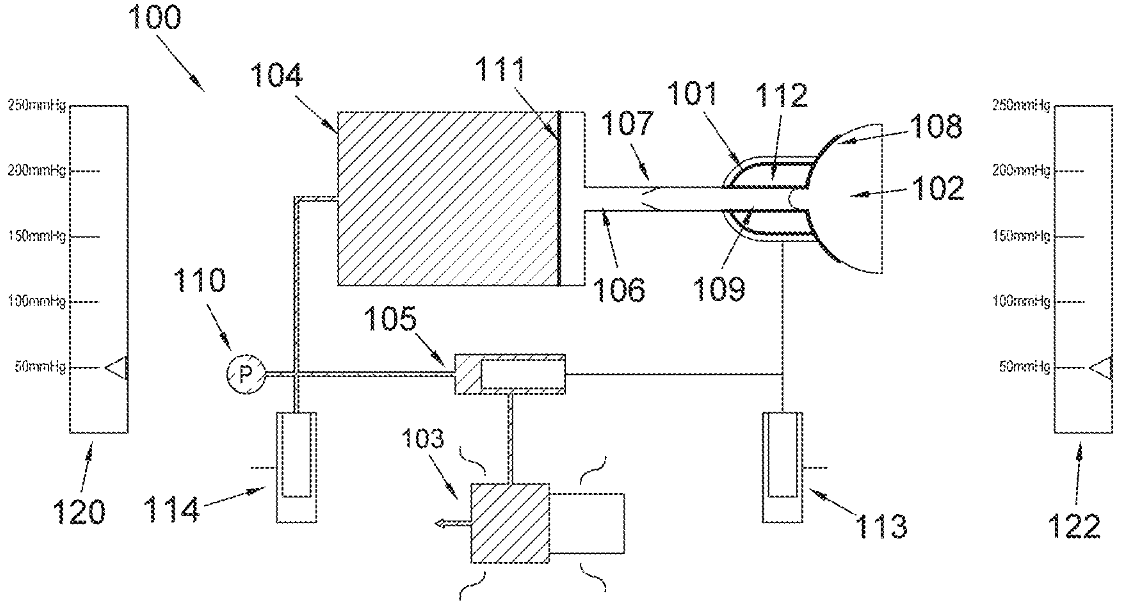
FIG. 4 shows a breast pump where a milk container and a nipple tunnel is evacuated of air to generate a base level vacuum according to an embodiment of the invention.

FIG. 4 shows this process and shows the breast pump 100 where a milk container 104 and a nipple tunnel 109 have been evacuated of fluid to generate a base level vacuum. The first diaphragm 111 is pulled away from its rest position and into the milk container 104. The base level vacuum and pulling force from the first diaphragm 111 removes any excess air from the nipple tunnel 109 and causes the second diaphragm 112 to contract around the breast, as shown in the transition from FIGS. 4 to 5. The base level vacuum is defined by a constant pressure lower than the atmospheric pressure and the pressure change caused by the base level vacuum (i.e. negative base level vacuum pressure) causes the second diaphragm 112 to contract around the breast.

Once the air pump 103 is turned on, the air pressure inside the milk container 104 and nipple tunnel 109 fall to the desired base level vacuum pressure, as shown on the first 120 and second 122 scales in FIG. 4. During the first mode, the air pump 103 is configured to pump at a first level to generate the base level vacuum desired pressure. The first level of pumping is configured to produce a negative air pressure of approximately −50 mmHg (relative to atmospheric pressure) inside the nipple tunnel 109.

Figure 5:
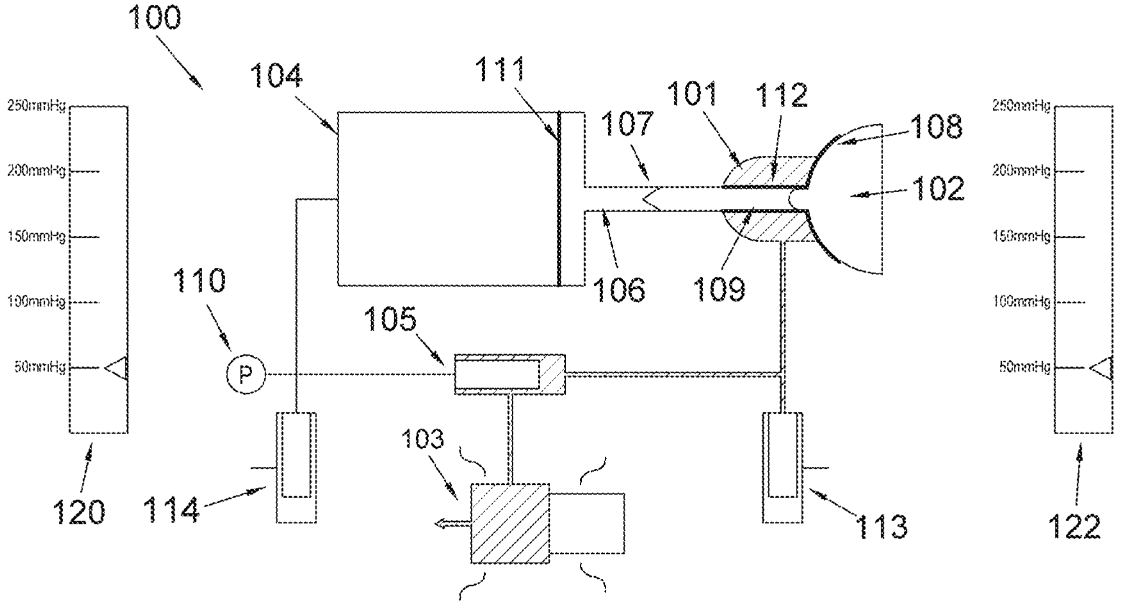
FIG. 5 shows a breast pump with the three-way solenoid valve switching settings again according to an embodiment of the invention.

Subsequently, as shown in FIG. 5 the three-way solenoid valve 105 switches setting to the second mode (step 1606). In the second mode, the three-way solenoid valve 105 is configured to allow air to flow directly from the exterior of the nipple tunnel 109 to the air pump 103, however, no air is able to pass between the milk container 104 and the air pump 103. During this switching process the air pump 103 remains on and continues to pump at the first level of pumping. Alternatively, the air pump 103 may shut off altogether during the switching process. As explained above, due to the non-return valve 107 and the seal between the breast 102 and the breast shield 101, and, air does not enter the system and therefore even if the air pump is shut off, air does not enter the system and the base level vacuum is maintained.

Once the three-way solenoid valve 105 has switched from the first mode to the second mode, the air pump 103 begins pumping at a second level of pumping (step 1607). The second level of pumping is more intense than the first level. This is because a greater negative air pressure must be generated for when the air pump 103 is to stimulate and express milk from the user's breast 102, compared to when only the base level vacuum desired pressure is required. Therefore, the second level of pumping generates a pressure inside the nipple tunnel of, for example, approximately −200 mmHg (relative to atmospheric pressure).

Application of vacuum to the second diaphragm 112 (e.g. the flexible nipple tunnel 109) causes negative pressure within the nipple tunnel 109. Cycling the pressure within the nipple tunnel 109 stimulates and causes expression of breast milk.

Figure 6:
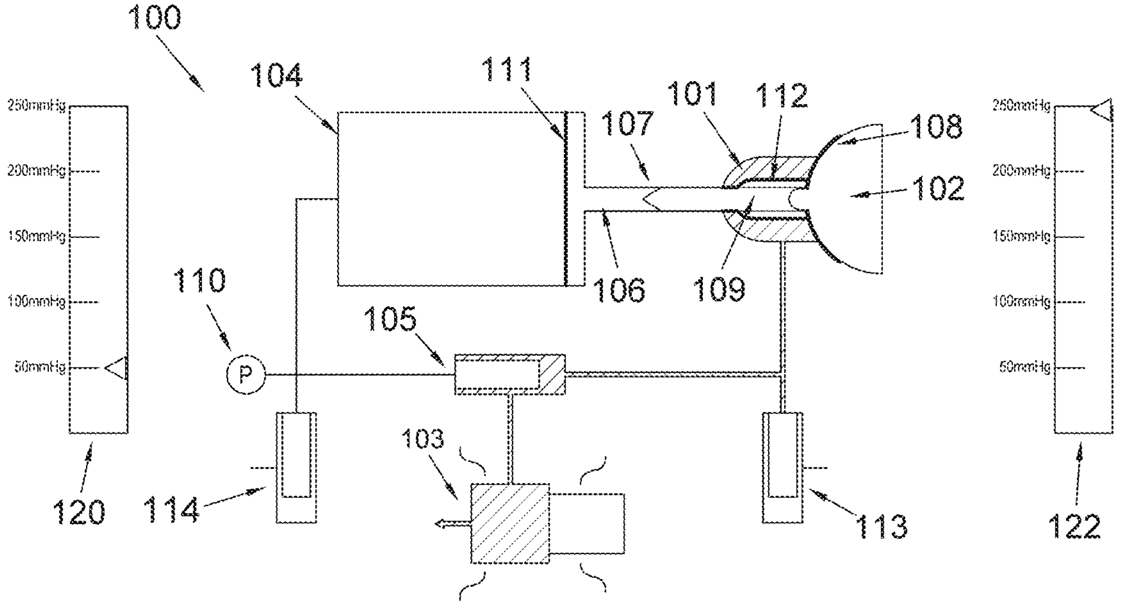
FIG. 6 shows a breast pump where the nipple tunnel is evacuated of air to stimulate a user's breast according to an embodiment of the invention.

When the three-way solenoid valve 105 is in the second mode, the air pump 103 starts pumping according to a milk expression program as dictated by a controller (not shown). The air pump 103 draws air outwards from the nipple tunnel 109 directly as shown in FIG. 6. This generates a negative air pressure surrounding the second diaphragm 112. There is no impact on the air pressure in the milk container 104, since the pathway from the air pump 103 to the milk container 104 is blocked by the positioning of the three-way solenoid valve 105 and the non-return valve (NRV) 107. As shown in FIG. 6, the nipple tunnel 109 is evacuated of air to stimulate a user's breast 102 according to the instructions of the predetermined control system (step 1608).

Figure 7:
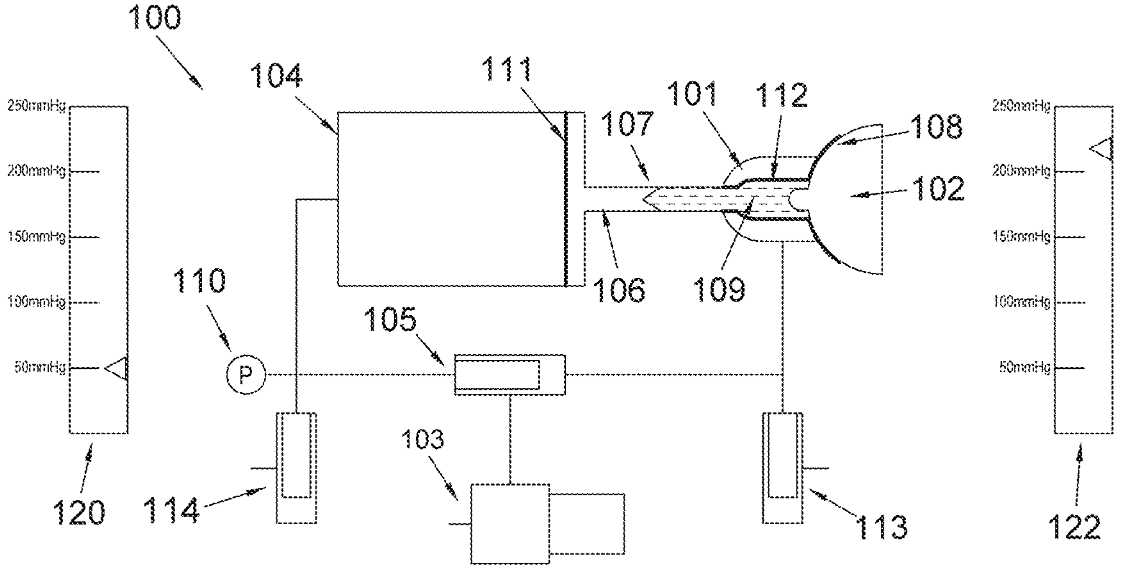
FIG. 7 shows milk expression using a breast pump according to an embodiment of the invention.

Once the three-way solenoid valve 105 switches to the second mode, the air pressure inside the nipple tunnel 109 falls further to the pressure that is desirable for pumping, as shown on the second 122 scale in FIG. 6. During the second mode, the air pump 103 is configured to pump at the second level to generate the desired pumping pressure (e.g. −200 mmHg relative to atmospheric pressure). Once the pumping pressure is applied, the breast tissue is stimulated, and the user gradually begins expressing milk into the nipple tunnel 109 (step 1609), as shown in FIG. 7. During this step additional biomimetic pumping sequences may be applied to the second diaphragm 112 to mimic the motion of a baby's mouth during breastfeeding. This may trigger the expression of milk or enhance the volume of milk produced.

The biomimetic motion may be achieved by using a flexible breast shield 101. The radially expanding nature of a flexible breast shield provides a sensation on the nipples which is different to traditional breast shields which expand the nipple axially. Radial expansion of the breast shield provides a sensation on the milk ducts of the nipple which is more similar to that of a baby feeding.

Once milk has expressed it remains in the nipple tunnel 109. Since there is now additional fluid in the nipple tunnel, the pressure in the nipple tunnel increases (i.e. becomes a smaller negative figure as shown in FIG. 7) compared to the negative pressure of the pumping vacuum pressure.

Figure 8:
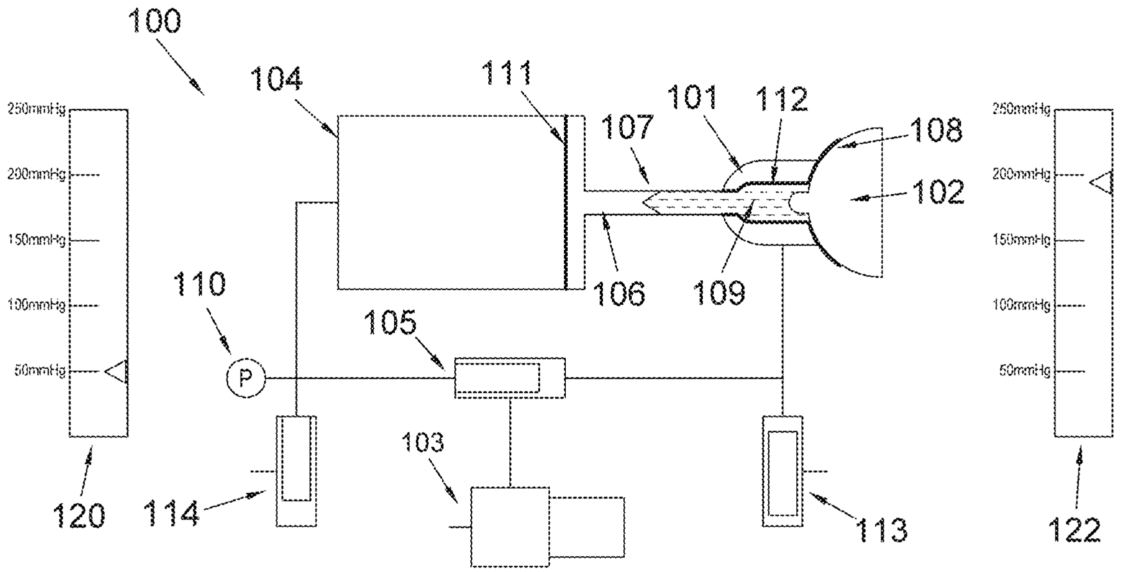
FIG. 8 shows the opening of a breast shield bleed solenoid valve in a breast pump according to an embodiment of the invention.
Figure 9:
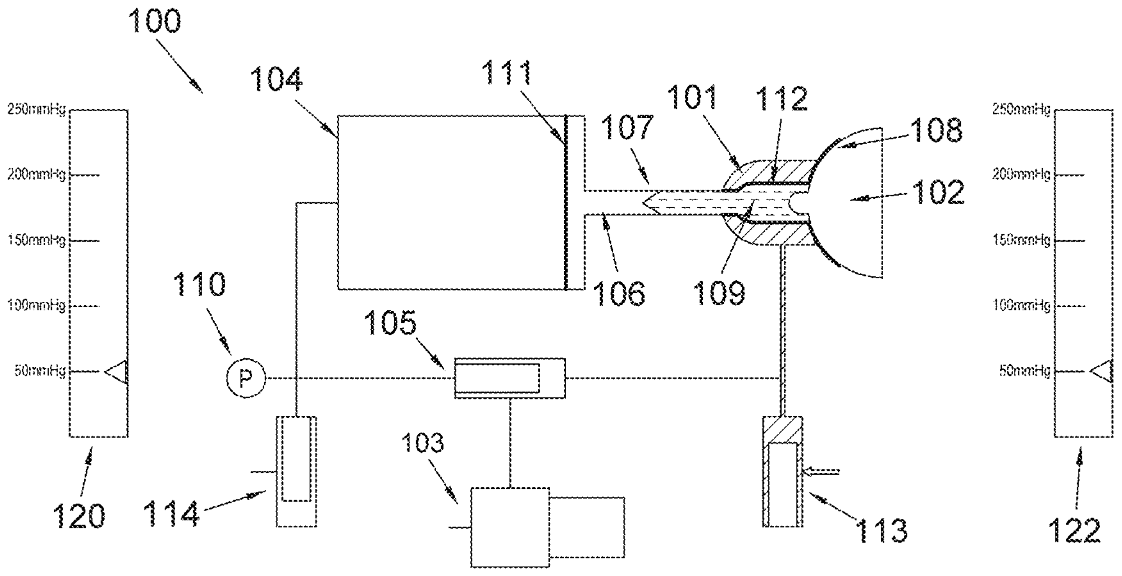
FIG. 9 shows the return of the nipple tunnel to a base level vacuum according to an embodiment of the invention.

Next, the bleed solenoid 113 is opened. During the expression phase, the opening of the bleed solenoid 113 provides a constant cycle of pumping vacuum followed by a rest. This is determined by a regular repeating cycle according to a pre-programmed control system. Once enough milk is expressed to fill the nipple tunnel 109, the pump stops pumping air from the system at the second level. Optionally, the air pump 103 may turn off altogether at this point in the cycle. The air pump 103 may stop before the bleed solenoid 113 is opened. As milk enters the nipple tunnel 109, the relative pressure increases compared to the milk bottle 104 when bleed solenoid 113 is open. This differential causes any milk to be pulled through the NRV 107 and into the milk bottle 104 thereby balancing the system and ultimately slightly reducing the base level vacuum. The opening of the bleed solenoid 113 is shown in FIG. 8 (step 1610). Once the bleed solenoid 113 is opened, the air pressure inside the nipple tunnel 109 returns to the base level vacuum pressure, as is shown in the second scale 122 in FIG. 9.

The vacuum is not released all the way back to atmospheric pressure as in other known breast pumps 100 and instead the base level vacuum is maintained to keep a constant seal of the breast shield 101 to the user's breast 102. A pressure sensor is used to measure the air pressure in the nipple tunnel. The bleed solenoid 113 is opened. Once the pressure reaches the base level vacuum pressure, the bleed solenoid 113 is closed and no further air enters the system, hence maintaining the base level vacuum inside the nipple tunnel 109. Pressure sensors are used to understand when base level vacuum drops as milk fills the nipple tunnel and flows into the milk container 104. The pressure sensors are also able to monitor when it is required to run a 'top up' cycle of the base level vacuum.

Figure 10:
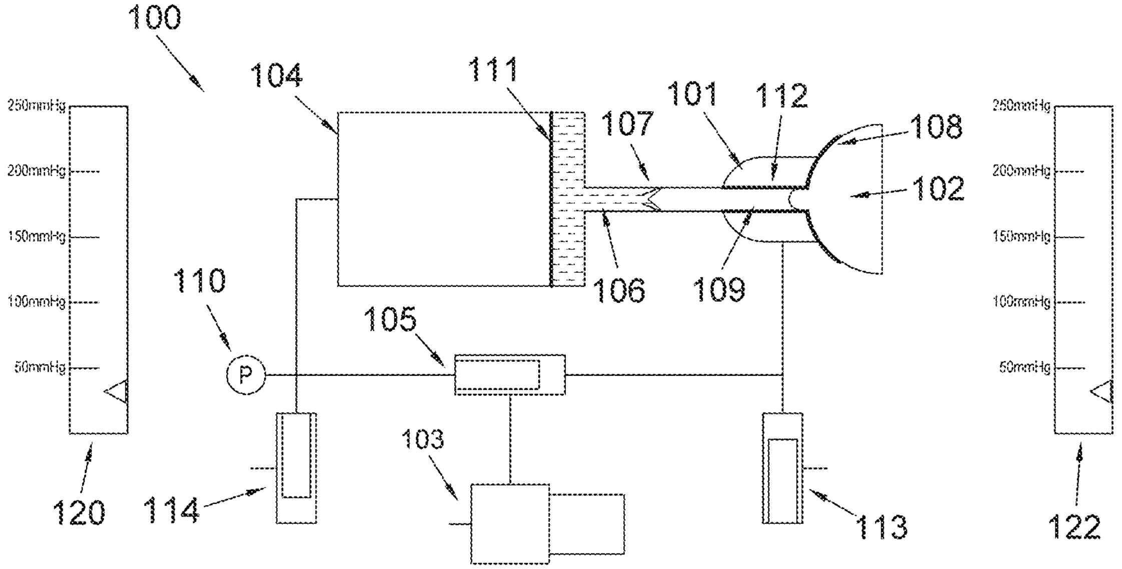
FIG. 10 shows the movement of milk from the nipple tunnel into the milk container according to an embodiment of the invention.

As it is expressed, the milk will flow from the nipple tunnel 109 through non-return valve 107 into the milk container 104, as shown in FIG. 10 (step 1611). This causes a slight rise in the pressure inside the milk container 104 as shown on the first scale 120. There is also a slight rise in the pressure inside the nipple tunnel 109 as shown on the second scale 122. The rise in pressure throughout the system is caused by the volume of milk which has entered the 'closed' system. This volume of milk takes up space in the closed system, hence increasing the magnitude of pressure inside the system. Once the milk has moved into the milk container 104, the bleed solenoid 113 is shut again to seal the air surrounding the second diaphragm 112 and nipple tunnel 109. The bleed solenoid 113 may shut as soon as the dry side of the nipple tunnel 109 (i.e. the side not facing the breast) returns to atmospheric pressure.

Milk is drawn from the nipple tunnel to the milk bottle by a slight increase in the pressure in the nipple tunnel 109 as it resets to a rest position when the pumping vacuum is no longer applied. This in turn opens the non-return valve 107 pushing milk into the milk container 107 until the point at which both sides of the system equalise again.

Figure 11:
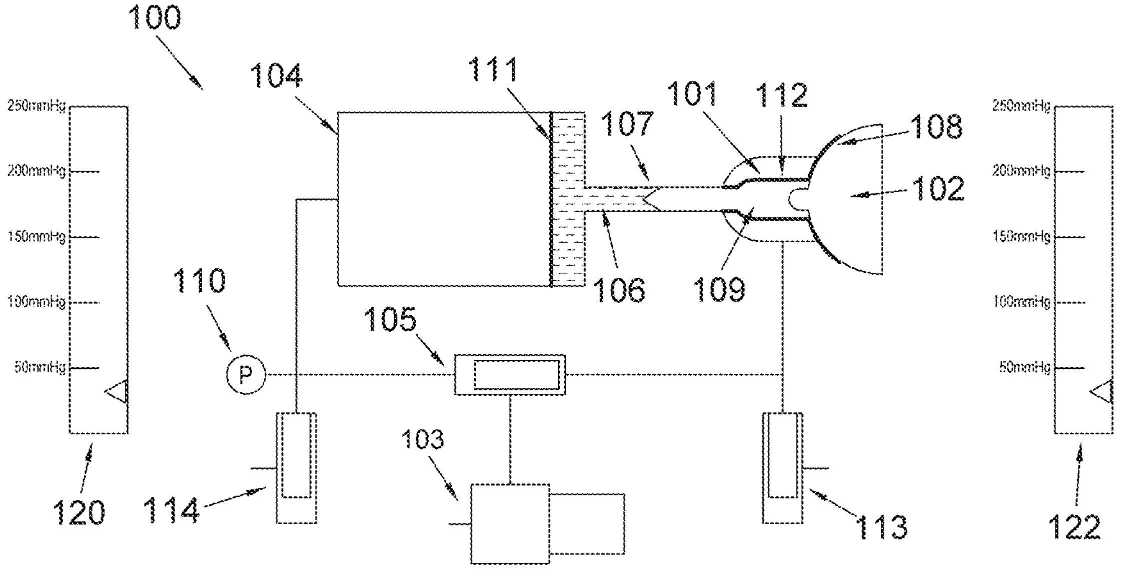
FIG. 11 shows the three-way solenoid valve switching settings again according to an embodiment of the invention.
Figure 12:
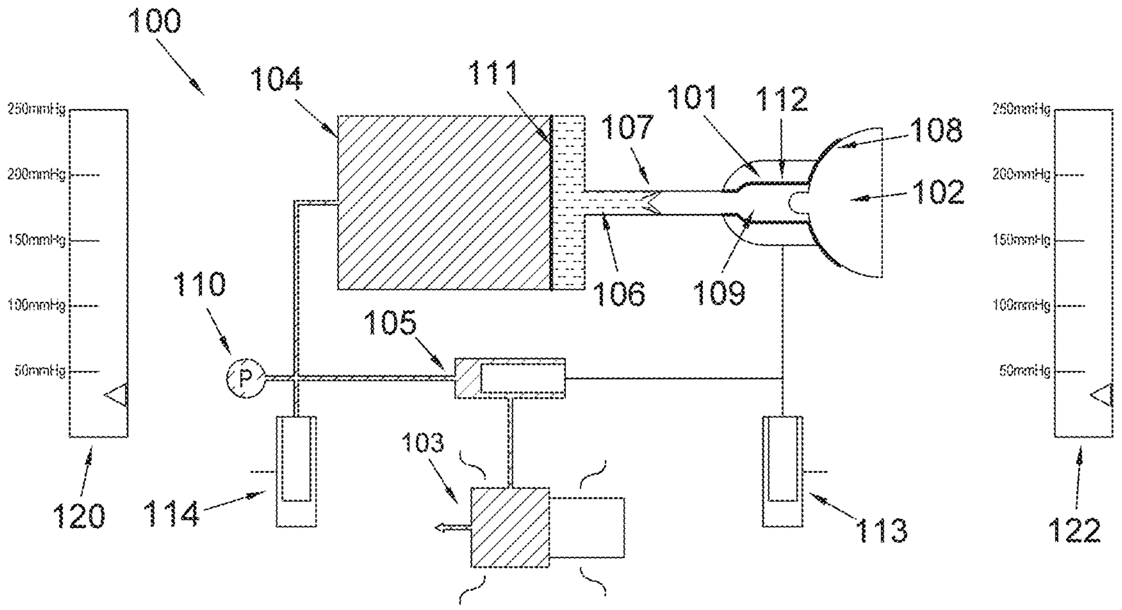
FIG. 12 shows the breast pump where a milk container and a nipple tunnel is evacuated of air to maintain a base level vacuum according to an embodiment of the invention.
Figure 13:
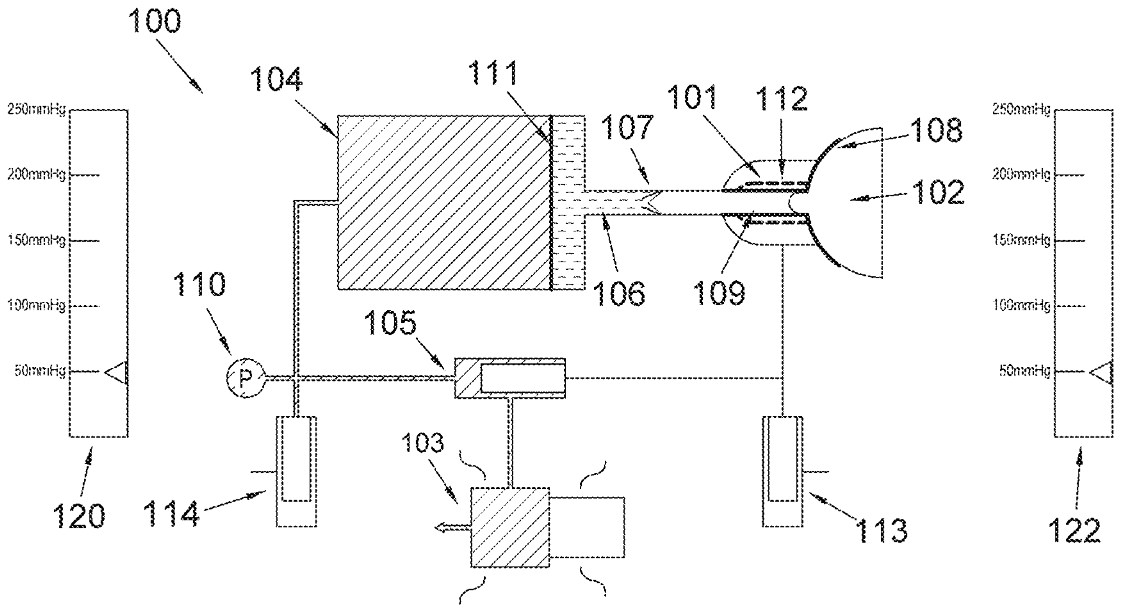
FIG. 13 shows the maintenance of a base level vacuum in the nipple tunnel according to an embodiment of the invention.

In order to maintain the base level vacuum and accommodate the small increase in pressure inside the milk container and nipple tunnel 109, a 'top-up' cycle is provided to extract further air from the system and to maintain the desired base level vacuum pressure. The same process previously described to generate the base level vacuum is repeated in the 'top up' cycle. To achieve this the three-way solenoid valve 105 switches back to the first mode, as shown in FIG. 11 (step 1612). Similar to previously, the three-way solenoid valve 105 is therefore configured to allow air to flow from the air pump 103 side of the first diaphragm 111 to the air pump 103. Next, the air pump 103 turns on according to the first mode (step 1613) and air is evacuated from the milk container 104, as shown in FIGS. 12 and 13. The air pump 103 may pump for a shorter time than is needed to generate the initial base level vacuum, since only a 'top up' of negative pressure is required. Air is again drawn from the nipple tunnel 109, through the non-return valve 107 and into the milk container 104. This movement is similarly achieved by the pulling action of the first diaphragm 111.

The pressure sensor 110 is used, as before, to determine that the air pressure inside the milk container 104 is at the desired base level vacuum pressure. As similarly described in relation to FIG. 3, fluid (i.e. air and/or milk) is also evacuated from the nipple tunnel 109 of the breast shield 101 during this process. The desired base level vacuum negative air pressure is generated in the milk container 104 and nipple tunnel 109 as shown on the first 120 and second 122 scales in FIG. 12. Using this process, a constant base level vacuum is maintained throughout a whole breast pumping session (step 1614). Once step 1614 is reached, the system is in the same state as is shown in 1603 with some milk present in the milk container 104. The process continues again from steps 1603 to 1613 to collect more milk in the milk container 104 until the pumping process is complete.

Overall, the three-way solenoid valve (or alternative switching means) can selectively pump the first and second diaphragms independently.

Graphical Evidence of Base Level Vacuum

Figure 17:
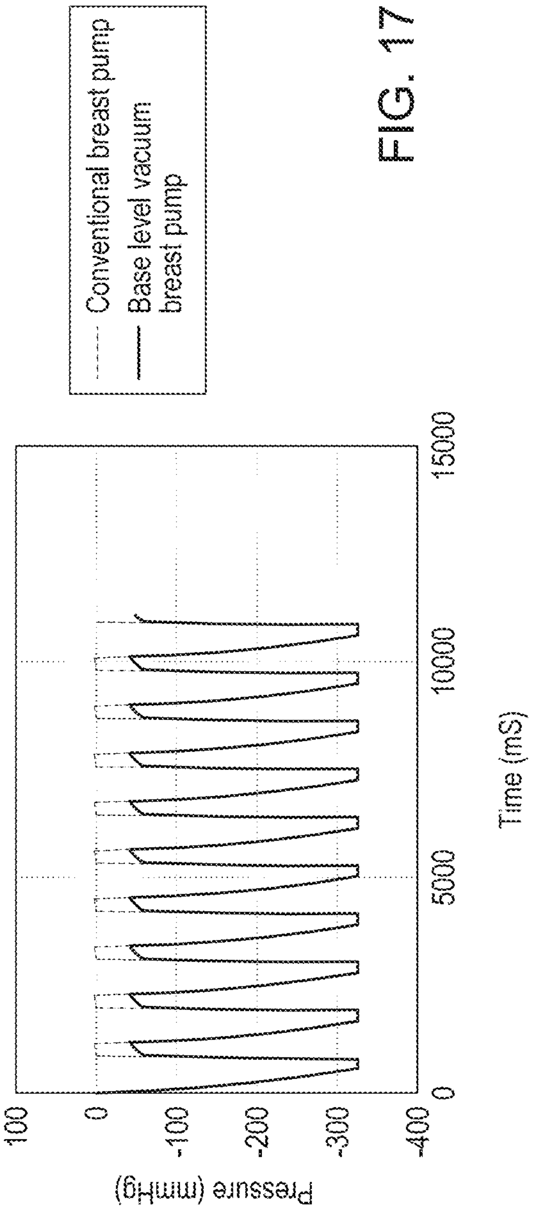
FIG. 17 shows a plot of the pressure inside the nipple tunnel for a conventional breast pump and a breast pump employing the base level vacuum of an embodiment of the invention.

FIG. 17 shows a plot of the pressure inside the nipple tunnel for a conventional breast pump and a breast pump employing the base level vacuum of some embodiments of the present invention.

The base level vacuum breast pump shows how the pressure inside the nipple tunnel 109 never returns to atmospheric pressure. Instead, a low level vacuum of −50 to −60 mmHg (relative to atmospheric pressure) is held in the nipple tunnel. Therefore, the pressure in the nipple chamber never returns to air pressure. The plot in FIG. 17 shows that the base level vacuum in the nipple tunnel 109 is highly consistent from one cycle to the next. In contrast the conventional breast pump returns to atmospheric pressure after each cycle.

As the pressure in the nipple tunnel 109 returns to the base level vacuum pressure, there is a visible decay in the vacuum being held in the nipple chamber. This may be caused by a leak in the system or by the movement of milk into the system. The 'top up' cycle seeks to return the pressure in the nipple chamber 109 to the desired base level vacuum pressure.

Software and Connect Devices

Figure 18:
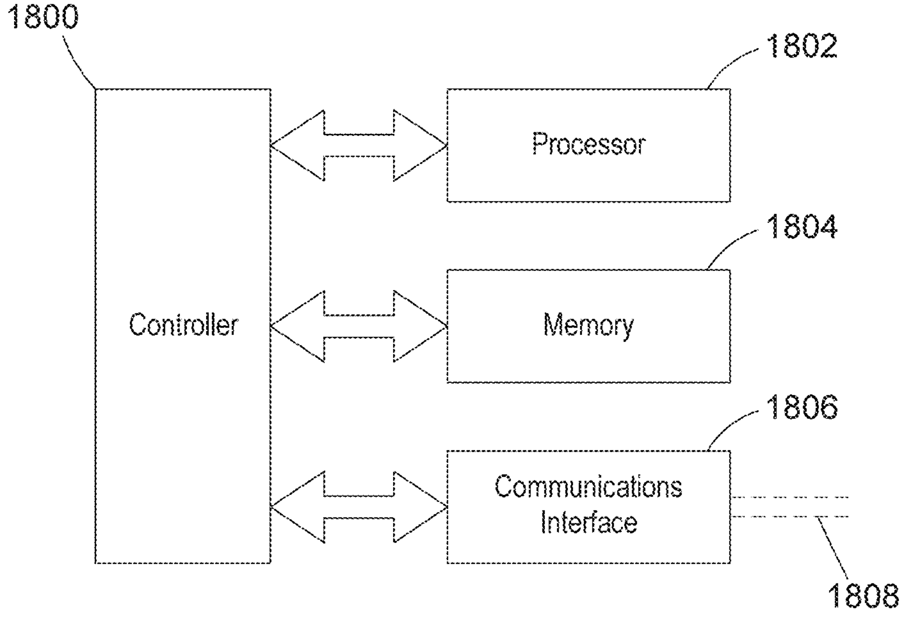
FIG. 18 shows a controller according to an embodiment of the invention.

The methods described herein may be implemented by one or more controllers such as a controller 1800 shown in FIG. 18, comprising one or more processors such as a processor 1802. The processor 1802 comprises computer-executable instructions, or a 'computer program', which, when executed, cause the controller to perform the methods disclosed herein. The computer program may comprise computer executable code or instructions arranged to instruct a computer to perform the functions of one or more of the methods described above. The computer program and/or the code or instructions for performing such methods may be provided to an apparatus, such as a computer, on a tangible, non-transitory computer usable or readable medium or computer program product. The computer readable medium could be, for example, an electronic, magnetic, optical, electromagnetic, infrared, or semiconductor system, or a propagation medium for data transmission, for example for downloading the code over the Internet. Alternatively, the computer readable medium could take the form of a physical computer readable medium, such as a transitory or non-transitory physical computer readable medium such as semiconductor or solid-state memory, magnetic tape, a removable computer diskette, a random-access memory (RAM), a read-only memory (ROM), a rigid magnetic disc, and an optical disk, such as a CD-ROM, CD-R/W or DVD.

Pump system related data may be sent by the system to a connected smartphone or other computer device. The data may be further analysed by a data analysis subsystem. The data may also be displayed on an application running on the computing device. The application may provide one or more of the following features: discreet and remote control of device, such as: play/pause, mode change, intensity setting change, battery life indication, session time and date tracking, milk volume tracking, integration with other devices, such as other breast pump system.

A remote control connected device will be used to allow the user of the breast pump to adjust the speed and pumping profile of the air pump. Changes in pumping profile may comprise differing patterns of long and short pulses and/or high and low intensity vacuum cycles.

Another exemplary configuration of the breast pump system will be described with reference to FIG. 19.

In the breast pump system 100 described in relation to FIGS. 1*a* to 13, there may be two bleed valves present. A bottle bleed valve 114 may be attached to the first channel 133 and a breast shield bleed valve 113 may be attached to the second channel 134. In the breast pump system 200 depicted in FIG. 19, there is only one bleed valve 214 present.

The operation of the breast pump 200 depicted in FIG. 19 is similar to the operation described in relation to the steps shown in FIGS. 1*a* to 13. The majority of the components may be the same as described in relation to FIGS. 1*a* to 13 and operate in a similar way.

The breast pump 200 of FIG. 19 may comprise: a breast shield 201, a milk container 204, an air pump 203, a first diaphragm 211 and a second diaphragm 212. The first diaphragm 211 is comprised within the housing of the breast pump 200. In one embodiment, the first diaphragm 211 may be located inside the milk container 204. In an alternative embodiment (not shown) the first diaphragm 211 may be located inside the housing of the breast pump 200 but not within the milk container 204.

The breast shield 201 comprises the second diaphragm 212. The second diaphragm 212 may comprise a breast flange 208 for fitting to the user's breast and a nipple tunnel 209 for receiving a nipple. The breast shield 201 comprises a first side 231 and a second side 232. The first side 231 of the breast shield 201 is the internal side and faces the user's breast when in use. The first side 231 of the breast shield 201 is configured to receive the user's breast. The second side 232 of the breast shield 201 is the external side and faces away from the user's breast when in use.

A non-return valve 207 is provided at the downstream end of the nipple tunnel 209. The non-return valve 207 is designed to allow fluid to pass in only one direction. The breast pump 100 may comprise at least one support means or tube 206 arranged internally to receive and hold the non-return valve 207.

The breast pump 200 comprises first 233 and second channels 234. The first channel 233 draws the base level vacuum on a first side 231 of the breast shield 201, applying a negative pressure to the inner walls of the nipple tunnel 209. The second channel 234 draws the pumping vacuum on a second side 232 of the breast shield 201, applying a negative pressure to the outer walls of the nipple tunnel.

The first channel 233 comprises, at least in part, a longitudinal path for receiving breast milk from the breast shield. The first channel 233 connects the air pump 203 to the first side 231 of the breast shield 201. The first channel 233 may also pass through the milk bottle 204. The first channel 233 extends to an internal portion of the breast shield 201 (i.e. the internal side which faces the user's breast when the pump is in use). The first channel 233 may extend to the first side 231 of the breast shield 201. The first channel 233 may extend into the nipple tunnel 209 of the breast shield 201.

The second channel 234 connects the air pump 203 to the second side, outer side, 232 of the breast shield 20. The second channel 234 may comprise a path extending outwardly from the breast shield 201. The radial path may be perpendicular to the longitudinal path for receiving breast milk from the breast shield. The second channel 234 does not pass through the milk container 204.

The first 233 and second channels 234 are independently controlled and are not connected to one-another. This allows a breast pump system to be generated which has an air pump 203 which alternately switches between delivering a base level vacuum and a pumping vacuum. The first channel 233 delivers the base level vacuum via the air pump 203 and the second channel 234 delivers the pumping vacuum via the same air pump 203. In some examples, applying the pumping vacuum to the external side of the breast shield (i.e. the external walls of the nipple tunnel) can cause radial expansion of the nipple tunnel, which mimics suction by a child's mouth. In other examples, the breast shield and nipple tunnel are rigid such that applying the pumping vacuum does not cause radial expansion of the nipple tunnel.

Similarly to FIGS. 1*a* to 13, two channels may be required to deliver the base level vacuum independently from the pumping vacuum.

Similarly to FIGS. 1*a* to 13, the breast pump 200 comprises a switching means to switch the breast pump between a first mode and a second mode to operate the first 211 and second 212 diaphragms respectively. That is to switch between use of the first channel 233 and the second channel 234. The switching means may comprise a three-way solenoid valve, as described below. Alternatively, the switching means may comprise two two-way solenoid valves. Alternative switching means are also feasible within the realms of what would be considered by a person skilled in the art.

A three-way solenoid valve 205 may be provided as part of the breast pump 200. The three-way solenoid valve 205 is a valve. The three-way solenoid valve 205 comprises two modes. In the first mode, the three-way solenoid valve 205 is configured to allow air to flow from the first diaphragm 211 to the air pump 203. In the second mode, the three-way solenoid valve 205 is configured to allow air to flow directly from the second diaphragm 212 to the air pump 203. Directly means that the air does not flow via the milk container 204. An embodiment of the three-way solenoid valve 205 is shown in FIGS. 15*a* and 15*b*.

As an alternative to using a three-way solenoid valve, two separate valves may be employed to achieve the same effect. Such valves may be solenoid valves or any other valve that is within the realms of what would be considered by a person skilled in the art. If two separate valves are provided as part of the breast pump 200, when they are connected in parallel they comprise two modes. In the first mode, a first valve 1503 is configured to allow air to flow from the milk container 204 to the air pump 203 (as shown in FIG. 15*c*). In the second mode, a second valve 1504 is configured to allow air to flow directly from the nipple tunnel 209 to the air pump 203 (as shown in FIG. 15*d*). Directly means that the air does not flow via the milk container 204

A bleed valve 214 may be provided. The bleed valve 214 is connected to the air pump 203. The bleed valve is connected to the three-way solenoid valve 205 on the air pump port side. The bleed valve 214 is connected to both the first channel 233 and the second channel 234, in a similar way as the air pump is connected to both the first channel 233 and the second channel 234. The bleed valve 214 may be a solenoid valve which has two ports. Alternative valves are also feasible within the realms of what would be considered by a person skilled in the art.

When the three-way solenoid valve 205 is switched to the first channel 233, the bleed valve 214 is configured to allow the first diaphragm 211 to return back to atmospheric pressure such as when measuring the volume of milk in the milk container or if the user wants to remove the breast pump. The bleed valve 214 allows a vacuum to be pumped from the first diaphragm 211 when the valve is 'closed'. When it is necessary to remove the pump or take a milk volume measurement, it is necessary to return to atmospheric pressure. This is achieved by turning the pump off and opening the bleed valve 214 which in turn allows air to rush back into the pump, re-pressurising it to atmospheric pressure.

When the three-way solenoid valve 205 is switched to the second channel 234 (i.e. the pumping vacuum), the bleed valve 214 is configured to reset the air pressure in the nipple tunnel to a base level vacuum when the air pump stops and ensure the breast pump 200 remains firmly attached to the user's breast. The bleed valve 214 is configured to open to release the pumping vacuum from the breast shield 201/second diaphragm 212. This allows air pressure in the nipple tunnel 209 and surrounding the first diaphragm 211 to return to the base level vacuum level rather than the pumping level. Using this configuration, the air pump 203 can remain on at all times, as the effect of the air pump 203 is neutralized by opening the bleed valve 214.

In an embodiment, the bleed valve 214 is provided to allow the milk container 204 to return back to atmospheric pressure such as when the user wants to remove the breast pump or alternatively remove the milk container 204 from the breast pump 200.

The bleed valve 214 also functions to allow an accurate milk volume measurement to be taken throughout the cycle, since it is required to reduce the vacuum in the milk container 204 to atmospheric pressure to obtain an accurate measurement of the milk volume collected in the milk container 204.

The use of one pump on both channels and only one bleed valve results in an efficient, small and compact breast pump that can be readily worn discreetly in bra.

Similarity to FIGS. 1*a* to 13, a pressure sensor 210 may be provided in the system. The pressure sensor 210 may be provided between the air pump 203 and the milk container 204. A second pressure sensor 202 may be provided between the air pump 203 and the breast shield 201.

Venting

The operation of the base level vacuum system described herein may also be improved by incorporating a further vent system to allow additional air in the system to be expelled.

Figure 20:
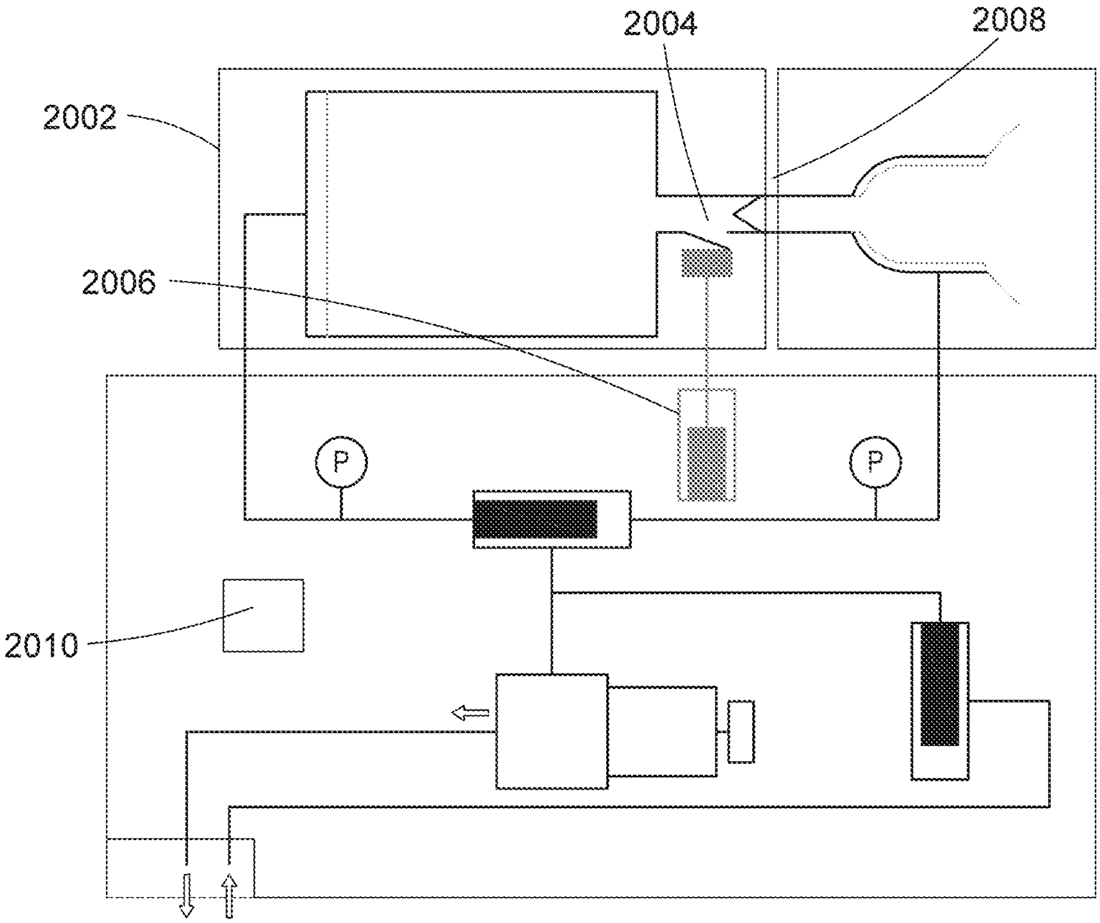
FIG. 20 shows a venting system according to an embodiment of the invention.

Reference will now be made to FIG. 20.

FIG. 20 depicts a milk container 2002 according to an embodiment of the present disclosure. The milk container 2002 comprises means for venting air. The means for venting air comprises a valve 2004 located on the wet side of the milk container and an actuator 2006 configured to open the valve.

The valve 2004 may be of any suitable type. One example valve is depicted in FIGS. 5A and 5B. The valve 2004 is located such that when the valve is open the wet side of the milk container is open to the atmosphere. In one example, the valve 404 is located near the non-return valve 2008 which is near the entrance to the milk container. In other examples, the valve 2004 is located in the body of the milk container 2002.

In some examples, the milk container 2002 comprises means for detecting the orientation 2010 of the milk container. The means for detecting the orientation 2010 of the milk container may be any suitable means. For example, an accelerometer, electronic gyroscope and/or an IR system. The IR system may comprise an IR transmitter and receiver, both located inside the milk container. At certain orientations, the milk will block or interfere with the transmitted IR. The IR system is configured to detect a change in orientation.

The means for detecting the orientation 2010 of the milk container is configured to determine if the milk container is within a predefined range of allowed orientations. In some embodiments, the milk container is configured to vent the air only when the milk container is in the allowed orientations. For example, the allowed orientations may be where the user is upright or near upright. If the user is outside the predefined range of allowed orientations, there is a risk of milk exiting the milk container via the means for venting air.

The actuator 2006 is configured to open the valve 2004 to control the process of venting. The actuator 2006 opens and closes the valve. Excess air held in the milk container is removed due to the diaphragm resetting to the level of the liquid in the bottle. When the dry side of the milk container is equalised to the atmosphere, the diaphragm provides a small positive pressure against the wet side. When the actuator 2006 opens the valve 2004, the small positive pressure is allowed to release. This resets the diaphragm and removes excess air until the diaphragm is restricted by the liquid in the bottle. In some embodiments, the diaphragm does not have enough spring force to displace the liquid, only air. That is, the diaphragm has a spring force low enough such that it will not displace liquid but high enough that it will displace excess air.

The actuator 2006 may be a solenoid actuator. Of course, any suitable actuator may be used. When the actuator 2006 closes the valve 2004, no air or indeed liquid can flow out of the valve. When the valve 2004 is closed the pressure in the milk container stays constant. The valve 2004 may be described as an active valve.

Figure 21A:
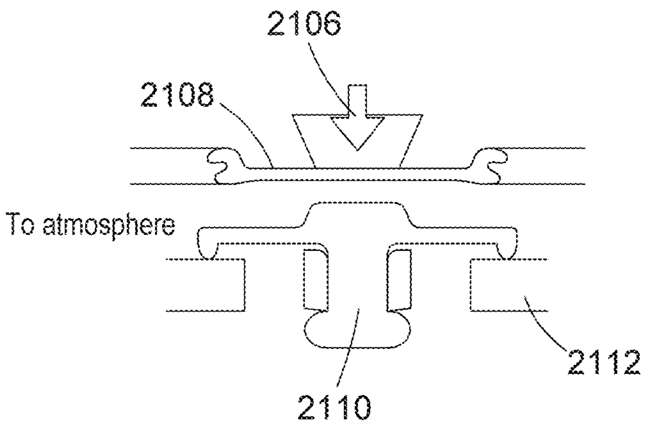
FIGS. 21A and 21B show a venting system according to an embodiment of the invention.
Figure 21B:
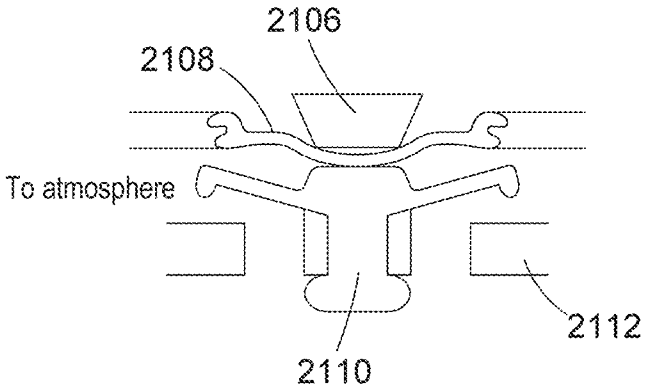

Reference will now be made to FIGS. 21A and 21B.

An example means for venting air comprising a valve located on the wet side of the container and an actuator configured to open the valve is depicted in FIGS. 21A and 21B.

The means for venting air may comprise: an actuator 2106, a flexible sealing portion 2108 and a valve portion 2110. FIG. 21A depicts the actuator 2106 at rest and the valve portion 2110 in the closed position. In the closed position, air is not being vented from the milk container. When the valve portion 2110 is closed, air cannot escape from the milk container. At rest, the actuator 2106 may be in contact with or in close proximity to the flexible sealing portion 2108.

FIG. 21B depicts the actuator 2106 in an engaged position which causes the valve portion 2110 to be in the open position. In the open position, air is vented from the milk container. When the actuator 2106 is engaged, the actuator 2106 makes contact with the flexible sealing portion 2108, flexing the flexible sealing portion 2108 and flexing the valve portion 2110. When flexed, the valve portion 2110 is open, allowing air to escape from the milk container. In the open position, air is vented from the milk container via an air channel between the flexible sealing portion 2108 and the milk container wall 2112. The air channel connects to the atmosphere external to the breast pump system.

Figure 22:
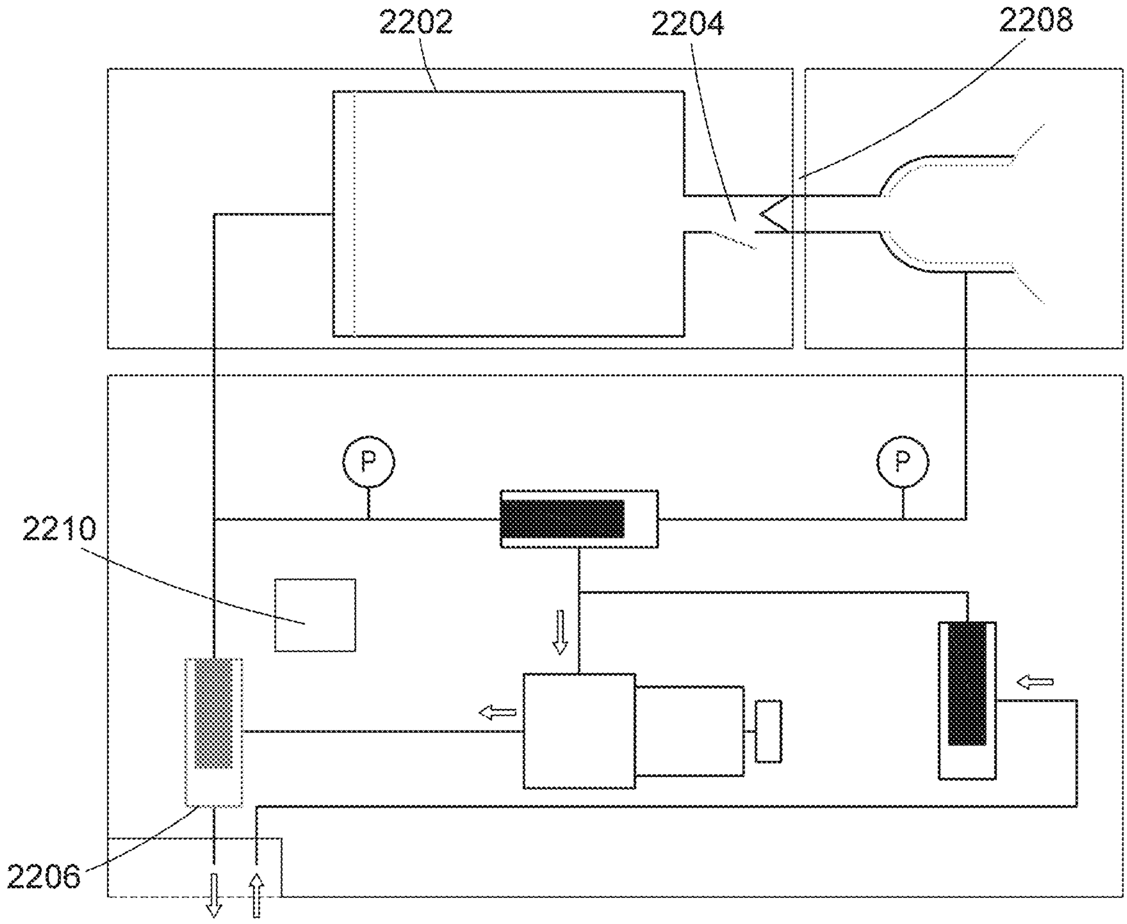
FIG. 22 shows a venting system according to an embodiment of the invention.

Reference will now be made to FIG. 22.

FIG. 22 depicts a milk container 2202 according to an embodiment of the present disclosure. The milk container 2202 comprises means for venting air. The means for venting air comprises a valve 2204 located on the wet side of the container configured to open in response to air applied to the dry side of the container.

The breast pump system may also comprise a means for pressuring the milk container 2206. For example, the means for pressuring the milk container 2206 may be a solenoid. The means for pressuring the milk container 2206 may be a pump connected to the dry side of the milk container. The means for pressuring the milk container 2206 may be configured to increase the pressure on the dry side of the milk container. This causes the dry side to increase in volume, causing the wet side to decrease in volume and vent out air from the milk container and towards the non-return valve 2208. The vented air can escape through the valve 2204, such as a non-return valve, flap valve, membrane microvalve, ball microvalve, etc. The valve 2204 is a one-way valve which is configured to only allow vented air from the milk container to escape. The valve 2204 does not let atmospheric air enter the system.

In some examples, the milk container 2202 comprises means for detecting the orientation 2210 of the milk container. The means for detecting the orientation 2210 of the milk container may operate in a similar way as described in relation to FIG. 8.

Figure 23:
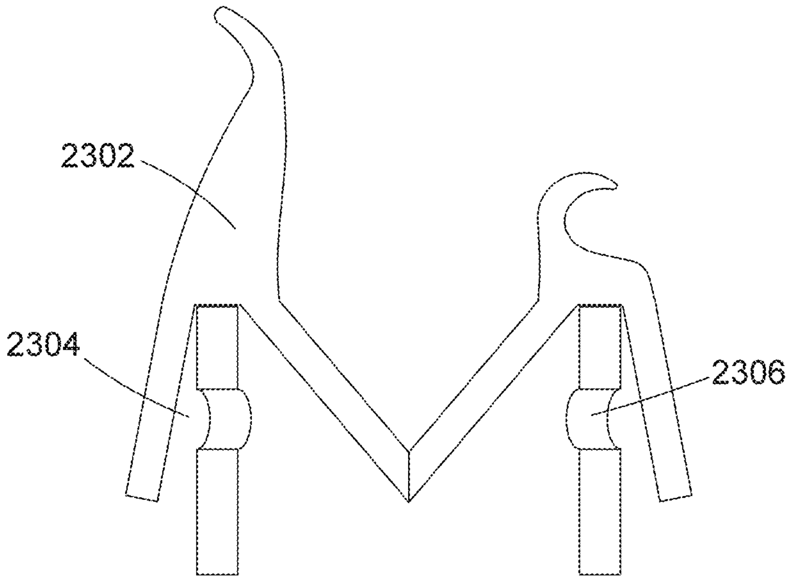
FIG. 23 shows a vent valve according to an embodiment of the invention.

Reference will now be made to FIG. 23.

In some examples, the valve 2204 located on the wet side of the container configured to open in response to air applied to the dry side of the container may be integrated into the non-return valve 1008. An example is depicted in FIG. 23. There is a first valve 2304 on one side of the wall of the nipple tunnel and a second valve 2306 on the opposite side of the nipple tunnel. The nipple tunnel may be defined as a channel between the milk container and the breast shield.

Figure 24:
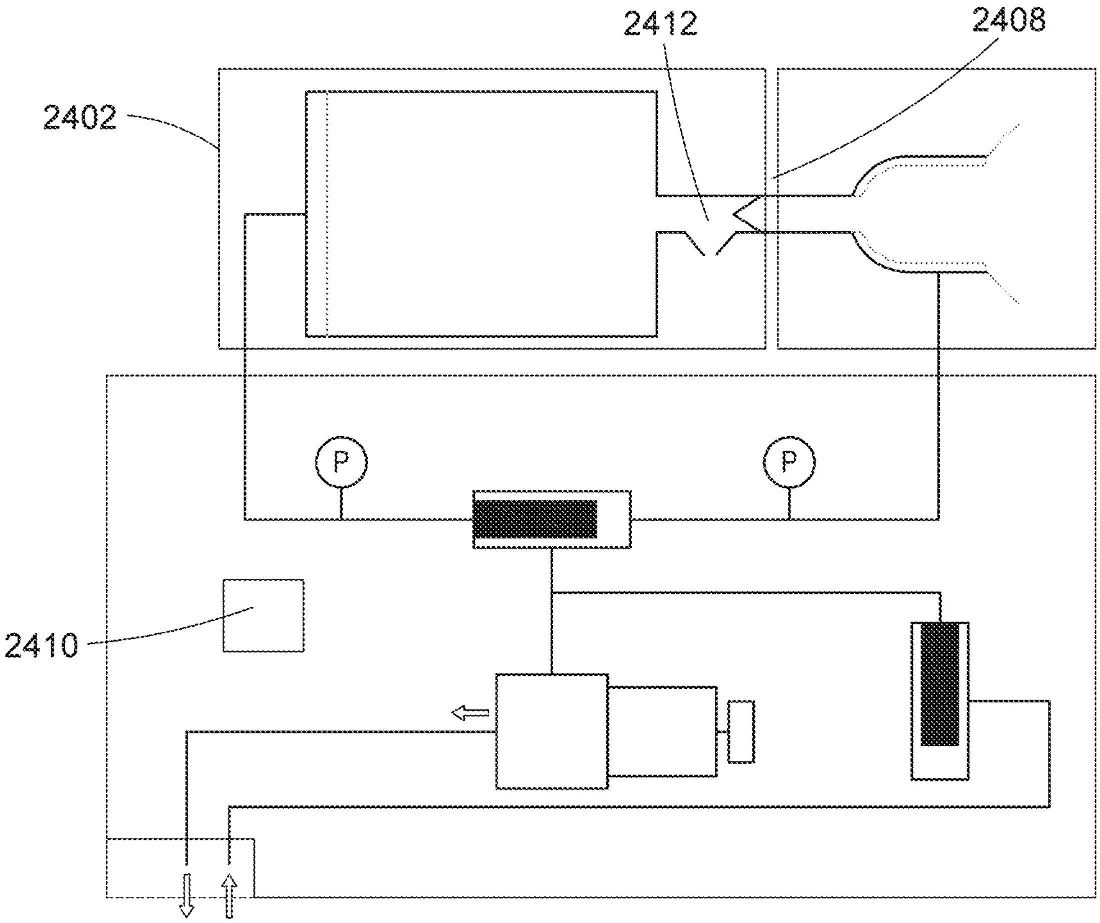
FIG. 24 shows a venting system according to an embodiment of the invention.

Reference will now be made to FIG. 24.

FIG. 24 depicts a milk container 2402 according to an embodiment of the present disclosure, wherein the means for venting air comprises a non-return valve 2412 located on the wet side of the container. The non-return valve 2412 may be described as the second non-return valve, an additional non-return valve to the first non-return valve 2408 which separates the milk container and breast shield. The non-return valve 2412 may be located on any suitable part of the wet side of the container.

The breast pump may be configured to pump the milk container 2402 to atmospheric pressure, such that excess air in the wet side is expelled via the non-return valve 2412. This configuration depicted in FIG. 24 is advantageous because it makes use of the breast pump's existing architecture without the need for additional components such as actuators or solenoids.

The non-return valve 2412 remains closed during a pumping phase of the operation of the breast pump. The non-return valve 2412 opens to expel excess air in the air venting phase of operation.

In some examples, the milk container 2402 comprises means for detecting the orientation 2410 of the milk container. The means for detecting the orientation 2410 of the milk container may operate in a similar way as described in relation to FIG. 4.

As described above, a milk-volume measurement process may measure the volume of milk and/or air in the milk container by changing the pressure or volume of the milk container. In one embodiment, the milk container 2402 may be configured to vent air from the non-return valve 2412 during the milk-volume measurement process. As the pressure or volume of the milk container changes, it may push out excess air which is expelled through the non-return valve 2412. This may occur every time the milk-volume measurement process is run.

Figure 25:
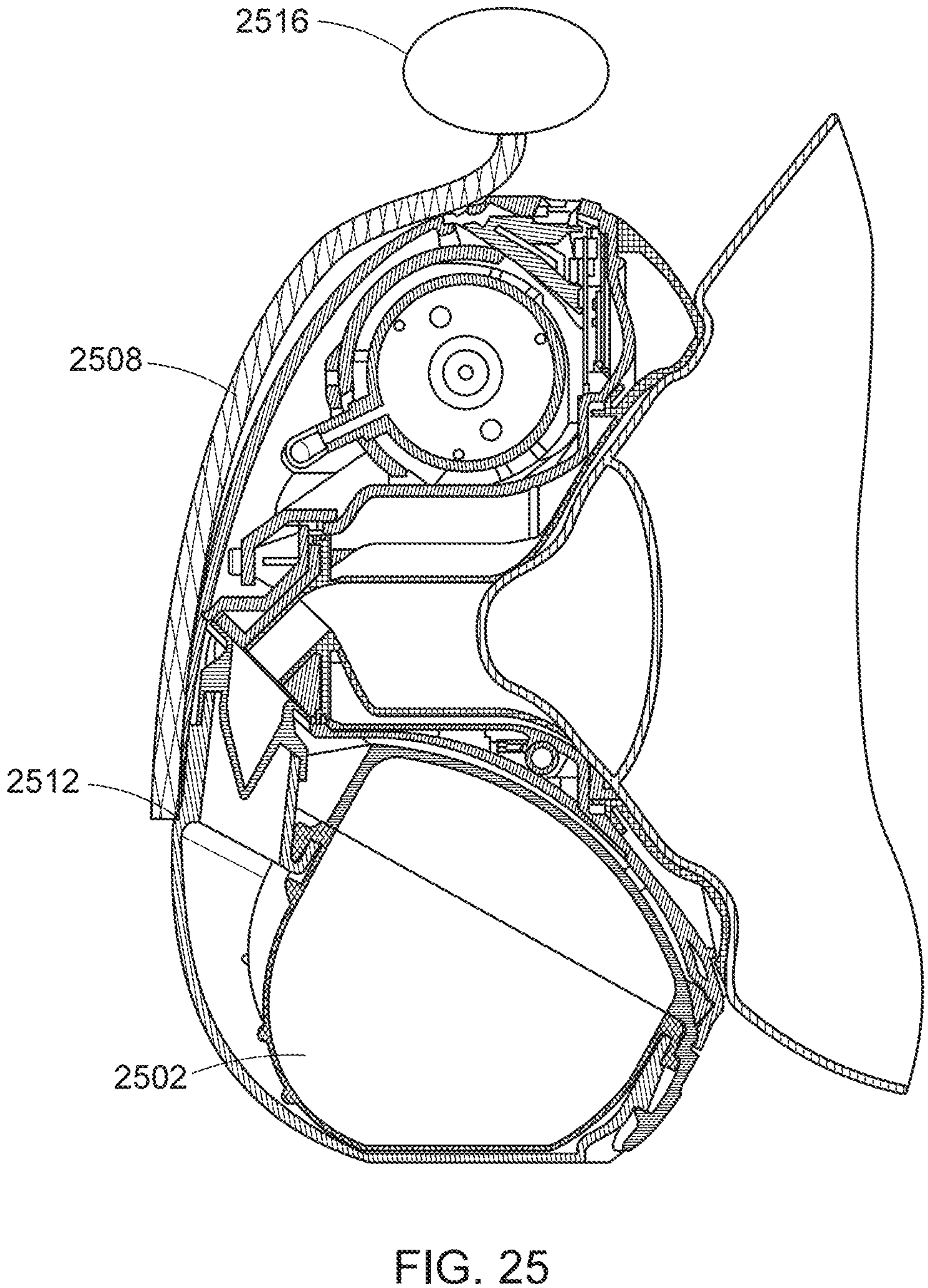
FIG. 25 shows a venting system according to an embodiment of the invention.

Reference will now be made to FIG. 25.

FIG. 25 depicts a milk container 2502 according to an embodiment of the present disclosure, wherein the means for venting air comprises an opening 2512 on the wet side, a tube 2508 connected to the opening, and a valve 2516 connected to the tube and located on an external side of the breast pump, wherein the valve is configured to be actuated by a user.

The valve 2516 is configured to be user accessible. For example, the valve 2516 may be located on the topmost point of the breast pump milk container system for easy access.

This configuration allows the user to relieve air pressure/excess air whilst pumping. Advantageously, this configuration can also allow for a quick decant of milk for high volume milk producer users. To decant, the user would need to actuate the valve 2516 and move the orientation of the system such that the milk flows from the milk container 2502 and out of the valve. The valve 2516 may be any suitable valve.

The milk container described thus far may comprise a flexible diaphragm located inside the milk container. In some embodiments, the flexible diaphragm forms part of a wall of the milk container. The flexible diaphragm forming part of a wall of the milk container will now be described.

Figure 26A:
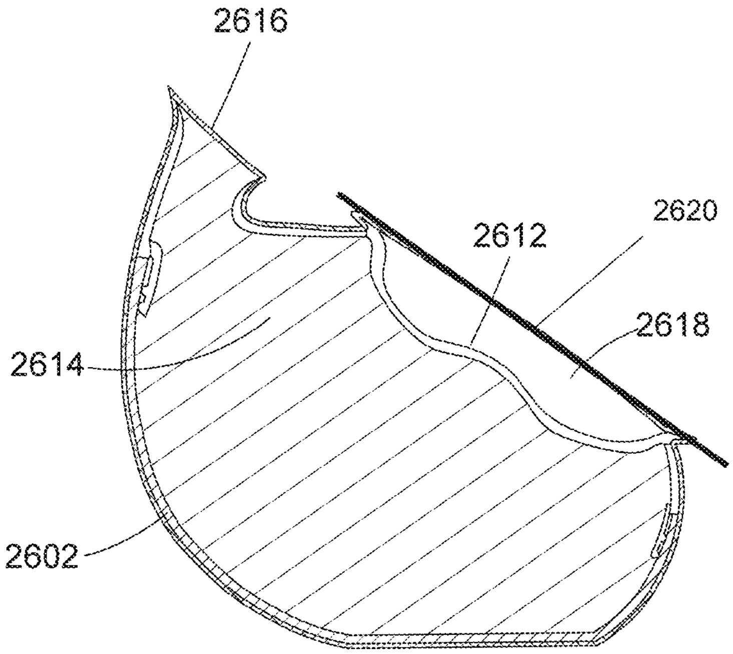
FIGS. 26A and 26B show a system according to an embodiment of the invention.
Figure 26B:
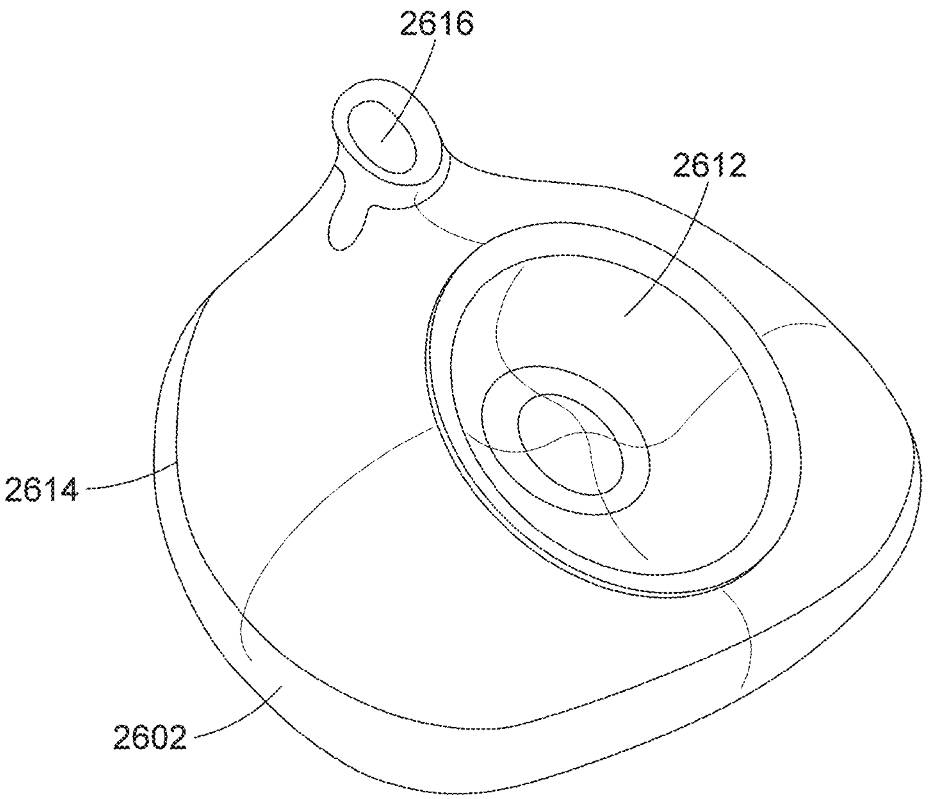

Reference will now be made to FIGS. 26A and 26B. FIG. 26A is a cross sectional view of a milk container 2602. FIG. 26B is a three dimensional view of the milk container 2602.

FIGS. 26A and 26B depict a milk container 2602 according to the present disclosure, wherein the flexible diaphragm forms part of a wall of the milk container. That is, the diaphragm forms part of an external wall of the milk container. In this embodiment, the "dry side" is external to the milk container and the "wet side" is internal to the milk container.

The flexible diaphragm is activated by an air pump applying negative pressure on the dry side of the diaphragm. In some examples, in a relaxed state the diaphragm has a non-flat profile, such as a curved or undulating profile. This enables the diaphragm to move without requiring the diaphragm material to stretch.

A milk container system is comprised of the milk container, the diaphragm forming part of the wall of the container, and an external portion which forms a chamber on the dry side of the diaphragm.

The wet side 2610 of the container is larger than the dry side 2618 of the container system. In FIG. 26A, the wet side 2614 is shown by the dashed area and the dry side 2618 as the non-dashed area. The dry side 2618 is not shown in FIG. 26B. The diaphragm 2612 may have a diameter smaller than the diameter of the milk container 2602. This configuration may be combined with any of the other embodiments described herein.

The diaphragm 2612 may form part of the exterior of the milk container 2602. That is, the diaphragm 2612 may form a wall of the milk container where one side of the diaphragm is internal to the milk container and the other side of the diaphragm is external to the milk container.

The diaphragm 2612 may be sealably attachable to the breast pump housing to form a dry chamber therebetween, defining the "dry side" of the diaphragm. An air pump pumps air into or from the dry chamber to engender movement in the diaphragm to create a suction in the milk container to draw breast milk into the milk container. The wet side and the dry side of the diaphragm in the embodiment in FIGS. 26A and 26B perform the same function as in the other embodiments disclosed herein, and therefore features of those embodiments apply to and can be combined with the embodiment in FIGS. 26A and 26B.

As described above, the breast pump may comprise a housing. A portion of the housing 2620 is illustrated in FIG. 26A. The diaphragm 2612 may be sealably attachable such that it forms a hermetic seal when attached to the housing. The diaphragm 2612 may be attachable such that it can be attached and unattached by the user. The dry chamber 2618 may be formed by the milk container and the housing. FIG. 26A shows the milk container 2602 attached to part of the housing 2620 such that the dry chamber 2618 is formed on the dry side of the diaphragm. FIG. 26B shows the milk container 2602 unattached to the housing such that no dry chamber is formed.

The milk container 2602 may meet the housing at a sealing lip, the sealing lip running circumferentially around the diaphragm. In some examples, the diaphragm comprises the sealing lip. In some examples, the milk container comprises the sealing lip on the wall which meets the diaphragm. The sealing lip may be configured to seal a flat surface 2620 of the housing to form the dry chamber 2618. In some examples, the housing of the breast pump has a flat surface 2620 for sealing to the milk container, such that one wall of the dry chamber is flat. In some examples, the housing has a curved section and a flat surface, where the flat surface abuts the sealing lip to form a seal. This creates a curved wall of the dry chamber 2618, which provide more room for the diaphragm to move into.

The diaphragm 2612 may be overmolded on the milk container to form the wet section 2614 inside the milk container, and the diaphragm sealably attached to the housing to form the dry chamber 2618.

As described above, the milk container 2602 may comprise the diaphragm 2612. The milk container may be removably attachable to the rest of the breast pump by a user. The diaphragm forms part of the milk container and is removably attachable from the breast pump with the other components of the milk container 2602, such that the user can empty milk from the container after a pumping session. The diaphragm 2612 may form part of a wall of the milk container 2602. In other words, the diaphragm 2612 may form part of the milk container surface. For example, the diaphragm 2612 may form around 50%, 30% or 10% of the milk container surface. Any suitable percentage of the milk container surface may be used.

The dry chamber 2618 may comprise a portion of the housing of the breast pump. That is the dry chamber 2618 may be part of the breast pump contained in the same housing as other components of the breast pump, for example, the air pump.

The milk container 2602 may comprise a first opening 2616 for receiving milk from the breast pump along a milk path. The first opening 2616 leads to the wet side. The milk path is similar to the milk path already described, for example the milk flows along the milk path through the breast shield and the nipple tunnel. The dry chamber 2618 may comprise a second opening for connection to an air pump. The second opening may be within the housing.

The first opening 2616 may be for pouring collected milk out of the milk container 2602. Alternatively, the milk container 2602 comprises a separate pouring opening for pouring collected milk out of the milk container.

The diaphragm forms part of the wall of the container. That is, the milk container, into which the milk flows from the milk path, is defined by a body forming walls around an internal chamber for collecting milk. The milk container is connectable to and removable from a milk path having a valve. Milk flows through a valve and into the milk container. The diaphragm forms a wall of the container and therefore is part of the body which is connectable to and removable from the milk path. In use, milk enters the milk container along a milk path, passing a valve before entering the milk container. The milk then collects in the milk container for the duration of the pumping session. The diaphragm forms part of the wall of the milk container. As milk collects in the container it touches the walls of the container. It may therefore fill up against the diaphragm.

The milk comprises an opening for receiving milk along a milk path and a main body for collecting milk. Milk is collected and stored in the main body during the pumping session. The diaphragm forms part of a wall of the main body of the milk container.

The diaphragm 2612 may be located on a portion of the milk container 2602 which, when the breast pump is positioned for use to receive milk from the user of the breast pump, forms a side or an upper portion of the milk container. FIG. 26A shows the breast pump positioned for use to receive milk from the user of the breast pump, this position can be considered upright. As shown in FIG. 26A, the diaphragm 2612 forms an upper portion of the milk container 2602.

In other embodiments, when the breast pump is positioned for use to receive milk from the user of the breast pump, the diaphragm forms a lower portion of the milk container. In these examples, the diaphragm may be configured to have enough spring force to overcome the pressure caused by the weight of the milk pressing down on the diaphragm.

The diaphragm 2612 may be located on the side of the milk container 2602 towards the user, when in its upright position. That is, the side of the milk container which is closer to the user's breast.

The milk container 2602 may have a flat bottom to allow the milk container to be stood on a surface. The diaphragm 2612 may form a side wall of the milk container, and may be on an upper portion of the milk container. That is, the diaphragm may be on a side wall on the upper half of the milk container. Alternatively, the diaphragm may form a top part of the milk container. In other embodiments, the diaphragm may be positioned elsewhere on the milk container.

The milk container 2602 may be a breast shaped hemispherical or half-ellipsoid shape, comprising a domed section and a flexible section. The domed section may be shaped to match or conform with the shape of a breast and/or bra. The shape of the milk container may be described as egg shaped or pebble shaped. The flexible section is the diaphragm 2612. The milk container 2602 may also comprise a substantially flat section at the bottom of the milk container such that the milk container can rest on a surface. In use, when worn by a user, the domed section may face outwards away from the user to conform with a bra. The bottom may be substantially flat, and the diaphragm may be positioned towards the user. The wall portion facing the user during use may be angled (i.e. not vertical).

In other examples, the diaphragm is located on other portions of the milk container. The diaphragm may be positioned in any conceivable location forming a portion of the wall of the main body of the milk container.

The milk container 2602 defines a main internal chamber, and the diaphragm 2612 forms part of the walls of the main internal chamber. That is, the diaphragm forms part of a wall of the main body of the milk container.

The milk container 2602 may comprise a rigid body and a hole, the hole sealed by the diaphragm 2612. Therefore, the walls of the milk container 2602 may comprise a rigid portion (the rigid body) and a flexible portion (the diaphragm 2612). The hole may be substantially the same shape and size as the diaphragm 2612. The hole may be hermetically sealed by the diaphragm 2612.

The diaphragm may be overmolded on the rigid portion of the container, or other forms of attaching the diaphragm to the rigid portions of the container may be used. The diaphragm 2612 may be substantially round, circle and/or oval shaped. The diaphragm 2612 may be a hemispherical bowl shape, a spherical dome and/or a spherical dome shape.

The diaphragm 2612 may be configured to be activated by low air pressure. The diaphragm 2612 may deform under low air pressure, transferring pressure from one side of the diaphragm to the other side. The diaphragm 2612 may oscillate it's position with air pump cycles as the pressure cycles from a higher pressure to a lower pressure.

FIG. 26A shows the milk container 2602 empty of milk. The wet side 2614 forms the entire inside of the milk container 2602. When the milk container 2602 is empty of milk, the wet side 2614 makes up the majority of the total volume of the milk container system while the dry chamber 2618 makes up a smaller volume of the milk container system. Due to the size of the wet side 2614 and the fact it makes up the entire milk container, there is a large amount of air in the wet side when the milk container 2602 is empty of milk.

When milk fills the milk container, the size of the wet side 2614 may increase due to an increased combined volume of air and milk. In turn, the dry side (aka the dry chamber 2618) may decrease in size. This happens by the diaphragm moving outwards from the wet side and into the dry side, hence decreasing the volume of the dry chamber and increasing the volume of the wet side.

Given there is air in the container (i.e. in the wet side) at the beginning of the pumping process, this air takes up internal volume which could otherwise be filled with milk. In order to reach maximum milk capacity of the milk container 2602, so that the container holds much milk as possible, air needs to be vented out of the wet side 2614 in order to make space for the milk. When at maximum capacity of milk, the total volume of the milk container 2602 will be substantially full of milk.

When milk fills the milk container, the size of the wet side 1414 may increase due to an increased volume of both air and milk. In turn, the dry side 2618 may decrease in size. In order to reach the maximum milk capacity of the milk container 2602, air needs to be vented out of the wet side 2614 in order to make space for the milk. When at maximum capacity of milk, the total volume of the milk container 2602 will be substantially full of milk. Air may be vented out according to any configuration and/or method described with reference to FIGS. 20 to 25. As described with reference to FIGS. 8 to 13, air may be vented multiple times throughout a pumping session.

Advantages

The non-return valves provided herein may have a small cracking pressure to overcome. This makes the milk container resilient to leaks even when there is no vacuum inside the container. This is useful, for example, when the pump is off but the bottle is full of milk and the vent valve is covered by milk. If there were no cracking pressure, just the weight of the milk would be enough for it to open and milk could leak out. If there is a cracking pressure, the valve will remain shut unless the pressure inside the bottle is greater than the cracking pressure.

Throughout the description it is described that air is vented out. However, more broadly, it is possible to vent out any positive pressure according to an embodiment of the present disclosure.

Embodiments of the disclosed wearable breast pump system may be configured to provide one or more of the following advantageous effects. The base level vacuum may reduce the amount of air present in the overall pumping system, since there is a reduced level of air in the nipple tunnel compared to when a system without a base level vacuum is used. This means that the air pump may not be required to work as hard in each pumping cycle and increases the efficiency of the pumping system. In turn, this may allow for improved battery lifetime. The noise level of the air pump may also be reduced.

The base level vacuum system may also reduce the likelihood of milk leaking from the breast pump during use. The base level vacuum may ensure constant suction of the breast shield to the nipple and breast, meaning that contact is maintained even when the standard pumping vacuum is not being applied. This constant suction may also allow the user to pump whilst bending or lying down since the breast shield is fixed to the user's breast.

The base level vacuum provided by some embodiments of the disclosed invention may provide a more precise base level vacuum and peak vacuum compared to previously known breast pump. By using sensors to constantly monitor the base level vacuum and pressure on the diaphragms, the target peak pressure may be more accurately achieved. Additionally, the pump and method provided may result in a breast pump that can more easily be applied to breasts and nipples of differing shapes and sizes, since the base level vacuum is drawn via a different pathway to the pumping vacuum.

The breast pump provided may be a compact in-bra wearable device which is quiet in operation and may be controlled from a connected device. This may provide a more discrete breast pump compared to previous known breast pumps. In particular, the user of the breast pump may wear the breast pump without the knowledge of people nearby, since both the shape, volume and ability to control the breast pump remotely from a connected device provide additional security to the user.

The breast pump provided may be configured as a self-contained, in-bra wearable device. The breast pump comprises an efficient assembly where the number of components are kept to a minimum. Additional components such as additional pumps, valves, tubes and sensors all add to the weight and bulkiness of the system. In examples where the second diaphragm is comprised within the milk container, space is saved in the system. In examples where there is only one pump present, space and weight of the system is reduced.

The breast pump of embodiments of the present disclosure provides a more efficient pumping cycle. The vacuum created in each pumping cycle is increased due to the presence of the base level vacuum. This is important for in-bra wearable breast pumps because it allows for a smaller pump to be used, which still provides a suitable level of vacuum. A smaller pump means that the entire breast pump device can be smaller and lighter and more readily fit within a bra. The more efficient, increased vacuum of embodiments of the present disclosure also allows for the pump to be run at a lower voltage and still provide a suitable level of vacuum. A pump run at a lower voltage means the breast pump is quieter with less vibration which results in improved discretion for the user. Discretion is particularly important for in-bra breast pumps because in-bra breast pumps are used in public places. For example, in-bra pumps are routinely used in places such as at work, at home during video call work meetings and in a car.

The connected device element may allow for a user adjustable base level vacuum to improve comfort. The breast pump may also provide improved comfort, since the base level vacuum improves comfort, due to the decrease in rubbing and friction between the breast shield and nipple because the breast shield is tightly fitted to the breast.

The breast pump may be easy to dry and clean since, it is ensured that only certain aspects of the device are held in contact with the milk lactated from the breast.

Features of the above aspects can be combined in any suitable manner. It will be understood that the above description is of specific embodiments by way of aspect only and that many modifications and alterations will be within the skilled person's reach and are intended to be covered by the scope of the appendant claims.

The disclosure includes the following clauses.

1. A breast pump, comprising:
an air pump for generating a base level vacuum and a pumping vacuum;
a breast shield for receiving a user's breast and comprising a first side and a second side;
a first channel for drawing the base level vacuum on the first side of the breast shield;
a second channel for drawing the pumping vacuum on the second side of the breast shield.

2. The breast pumping according to clause 1, wherein the first channel comprises a longitudinal path for receiving breast milk from the breast shield.

3. The breast pump according to any preceding clause, wherein the first channel extends to an internal portion of the breast shield.

4. The breast pump according to any of clauses 2 or 3, wherein the second channel comprises a radial path extending outwardly from the breast shield, and wherein the radial path is perpendicular to the longitudinal path.

5. The breast pump according to any preceding clause, wherein the air pump is configured to draw the base level vacuum on the first side of the breast shield and draw the pumping vacuum on the second side of the breast shield.

6. The breast pump according to any preceding clause, further comprising:
a first diaphragm configured to deliver the pumping vacuum, wherein the breast shield comprises the first diaphragm; and
a second diaphragm configured to deliver the base level vacuum.

7. The breast pump according to any preceding clause, wherein the breast shield comprises a nipple tunnel for receiving the user's nipple.

8. The breast pump according to clause 7, wherein the first channel extends into the nipple tunnel of the breast shield.

9. The breast pump according to any preceding clause, wherein in a first mode the air pump generates the base level vacuum along the first channel and in a second mode the air pump generates the pumping vacuum along the second channel.

10. The breast pump according to clause 9, wherein
in the first mode the air pump generates a base level vacuum in the breast shield; and
in the second mode the air pump generates a pumping vacuum in the breast shield.

11. The breast pump according to clause 10, wherein in the first mode the pressure inside the breast pump is less than atmospheric pressure.

12. The breast pump according to any preceding clause, wherein the pumping vacuum is stronger than the base level vacuum.

13. The breast pump according to any preceding clause, wherein the air pump is a piezo pump or rotary diaphragm pump or a positive displacement pump.

14. The breast pump according to any of clauses 6 to 13, wherein the second diaphragm is located within a housing of the breast pump.

15. The breast pump according to any preceding clause, further comprising a milk container for receiving milk and wherein the second diaphragm is comprised within the milk container.

16. The breast pump according to clause 15, in which the milk container is a re-useable milk container that is connected to a housing with a surface shaped to continue a curved or breast-like shape of the pump.

17. The breast pump according to clauses 15 or 16, comprising a non-return valve that permits milk to flow one way from the nipple tunnel to the milk container, and optionally wherein the non-return valve is flexible.

18. The breast pump according to clause 17, wherein the non-return valve self-seals under a pressure differential across an opening to the milk container.

19. The breast pump according to clauses 17 or 18, wherein the non-return valve is an umbrella valve or duck-bill valve or flap valve.

20. The breast pump according to any of clauses 9 to 19, comprising a three-way solenoid valve connected to the air pump and configured to switch between the first and second mode.

21. The breast pump according to clause 20, wherein in the first mode the three-way solenoid valve is configured to allow air to flow along the first channel; and in the second mode, the three-way solenoid valve is configured to allow air to flow along the second channel.

22. The breast pump according to any preceding clause, wherein the breast pump is configured as a self-contained, in-bra wearable device.

23. A method of operating a breast pump, comprising:

switching the breast pump to a first mode and using an air pump to generate a base level vacuum along a first channel;

switching the breast pump to a second mode and using the air pump to generate a pumping vacuum along a second channel.

24. The method of clause 23, wherein the first channel comprises a longitudinal path for receiving breast milk from the breast shield and the second channel comprises a radial path extending outwardly from the breast shield.

25. The method of clauses 23 or 24, wherein a first diaphragm delivers the pumping vacuum.

26. The method of any of clauses 23 to 25, wherein a second diaphragm delivers the base level vacuum.

27. The method of any of clauses 23 to 26, wherein a switching means is used to switch the breast pump between the first and second mode.

28. The method of clause 27, wherein the switching means is a three-way solenoid valve.

29. A non-transitory computer readable medium comprising computer executable instructions which, when executed by a processor, cause the processor to perform the method of clauses 23 to 28.

30. The breast pump of any of clauses 1 to 22, further comprising a processor configured to perform the method of any of claims 23-29.

B1. A method of operating a breast pump, comprising:

switching the breast pump to using an air pump to generate a base level vacuum along a first channel;

switching the breast pump to using the air pump to generate a pumping vacuum along a second channel.

B2. The method of clause B1, wherein the breast pump is in a first mode when the breast pump is using the air pump to generate the base level vacuum along the first channel; and wherein the breast pump is in a second mode when switching the breast pump to using the air pump to generate the pumping vacuum along the second channel.

B3. The method of clause B1 or B2, wherein the first channel comprises a longitudinal path for receiving breast milk from the breast shield and the second channel comprises a radial path extending outwardly from the breast shield.

B4. The method of any of clauses B1 to B3, wherein a first diaphragm delivers the pumping vacuum.

B5. The method of any of clauses B1 to B4, wherein a second diaphragm delivers the base level vacuum.

B6. The method of any of clauses B1 to B5, wherein a switching means is used to switch the breast pump between the first and second mode.

B7. The method of clause B6, wherein the switching means is a three-way solenoid valve.

B8. A computer readable medium comprising computer executable instructions which, when executed by a processor, cause the processor to perform the method of any of clauses B1 to B7.

B9. The method of any of clauses B1 to B7, wherein the method uses the breast pump of any of clauses 1 to 22.

The invention claimed is:

1. A wearable breast pump, comprising:

an air pump system configured to fit within a bra when the breast pump is worn, for generating a base level vacuum and a pumping vacuum;

a first flexible diaphragm configured to deform in response to negative air pressure to deliver the base level vacuum;

a breast shield for receiving a user's breast and comprising a first side and a second side;

a first channel for drawing the base level vacuum on the first side of the breast shield;

a second channel for drawing the pumping vacuum on the second side of the breast shield;

a first bleed solenoid connected to the first channel, wherein the first bleed solenoid is configured to allow the first channel to reach atmospheric pressure; and a second bleed solenoid connected to the second channel, wherein the second bleed solenoid is configured to allow the second channel to reach the same pressure as the first channel.

2. The breast pump of claim 1, wherein the first channel comprises a longitudinal path for receiving breast milk from the breast shield.

3. The breast pump of claim 2, wherein the second channel comprises a radial path extending outwardly from the breast shield, and wherein the radial path is at an angle to the longitudinal path.

4. The breast pump of claim 1, wherein the first channel extends to an internal portion of the breast shield.

5. The breast pump of claim 1, wherein the air pump system is configured to draw the base level vacuum on the first side of the breast shield and draw the pumping vacuum on the second side of the breast shield.

6. The breast pump of claim 1, wherein the breast shield comprises a second flexible diaphragm configured to deform in response to negative air pressure to deliver the pumping vacuum.

7. The breast pump of claim 1, wherein the breast shield comprises a nipple tunnel for receiving the user's nipple, wherein the first channel extends into the nipple tunnel of the breast shield.

8. The breast pump of claim 1, wherein in a first mode the air pump system generates the base level vacuum along the first channel, and in a second mode the air pump system generates the pumping vacuum along the second channel, wherein in the first mode the air pump system generates the base level vacuum in the breast shield, and wherein in the second mode the air pump system generates a pumping vacuum at the breast shield.

9. The breast pump of claim 8, wherein in the first mode the pressure inside the breast shield is less than atmospheric pressure.

10. The breast pump of claim 8, comprising a three-way solenoid valve connected to the air pump system and configured to switch between the first and second mode.

11. The breast pump of claim 10, wherein in the first mode the three-way solenoid valve is configured to allow air to flow along the first channel; and in the second mode, the three-way solenoid valve is configured to allow air to flow along the second channel.

12. The breast pump of claim 1, wherein the pumping vacuum is stronger than the base level vacuum.

13. The breast pump of claim 1, wherein the first diaphragm is located within a housing of the breast pump.

14. The breast pump of claim 1, further comprising a milk container for receiving milk, wherein the first diaphragm is completely located within the milk container.

15. The breast pump of claim 14, comprising a non-return valve that permits milk to flow one way from a nipple tunnel to the milk container, and optionally wherein the non-return valve is flexible.

16. The breast pump of claim 15, wherein the non-return valve self-seals under a pressure differential across an opening to the milk container.

17. The breast pump of claim 1, wherein the breast pump is configured as a self-contained, in-bra wearable device.

18. The breast pump of claim 1, wherein the air pump system comprises an air pump for generating the base level vacuum and the pumping vacuum.

19. The breast pump of claim 1, wherein the breast shield is flexible and configured to contract or expand radially based on the pumping vacuum.

20. A wearable breast pump, comprising:

an air pump system for generating a base level vacuum and a pumping vacuum;

a milk container configured to fit within a bra when the breast pump is worn;

a first flexible diaphragm completely located within the milk container and configured to deform in response to negative air pressure to deliver the base level vacuum;

a breast shield for receiving a user's breast and comprising a first side and a second side;

a first channel for drawing the base level vacuum on the first side of the breast shield; and a second channel for drawing the pumping vacuum on the second side of the breast shield;

wherein the breast shield comprises a second flexible diaphragm configured to deform in response to negative air pressure to deliver the pumping vacuum.

21. The breast pump of claim 20, wherein the breast shield is configured to contract or expand radially based on the pumping vacuum.

22. The breast pump of claim 20, wherein the pumping vacuum is stronger than the base level vacuum.

* * * * *